United States Patent [19]

Schenker

[11] Patent Number: 4,478,837
[45] Date of Patent: Oct. 23, 1984

[54] 3-HYDRAZINO CYCLOALKYL[C]PYRIDAZINES AS ANTIHYPERTENSIVE AGENTS

[75] Inventor: Erhard Schenker, Basel, Switzerland

[73] Assignee: Sandoz Ltd., Basel, Switzerland

[21] Appl. No.: 29,892

[22] Filed: Apr. 13, 1979

Related U.S. Application Data

[63] Continuation of Ser. No. 640,633, Dec. 15, 1975, abandoned, which is a continuation of Ser. No. 485,578, Jul. 3, 1974, Pat. No. 3,954,754, which is a continuation-in-part of Ser. No. 251,035, May 8, 1972, Pat. No. 3,838,125.

[30] Foreign Application Priority Data

| | | |
|---|---|---|
| May 11, 1971 [CH] | Switzerland | 6951/71 |
| May 11, 1971 [CH] | Switzerland | 6952/71 |
| May 26, 1971 [CH] | Switzerland | 7679/71 |
| May 26, 1971 [CH] | Switzerland | 7683/71 |
| May 28, 1971 [CH] | Switzerland | 7848/71 |
| May 28, 1971 [CH] | Switzerland | 7849/71 |
| Oct. 15, 1971 [CH] | Switzerland | 15120/71 |
| Oct. 15, 1971 [CH] | Switzerland | 15121/71 |

[51] Int. Cl.³ .............. C07D 237/28; C07D 237/26; A61K 31/50; A61K 31/495
[52] U.S. Cl. .................................................. 424/250
[58] Field of Search ........................................ 424/250

[56] References Cited

U.S. PATENT DOCUMENTS 3,838,125 9/1974 Shenker .......................... 424/250

Primary Examiner—Mark L. Berch
Attorney, Agent, or Firm—Gerald D. Sharkin; Robert S. Honor; Thomas O. McGovern

[57] ABSTRACT

Pharmaceutical compositions comprising as the active ingredient thereof an aminopyridazine derivative of the formula:

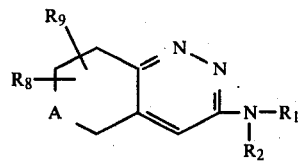

wherein
$R_1$ is amino, or

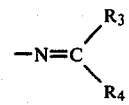

wherein each of
$R_3$ and $R_4$ is alkyl of 1 to 4 carbon atoms, or
$R_3$ and $R_4$ together with the carbon atom to which they are bound, form a cycloalkylidene radical of 5 to 12 carbon atoms,
$R_2$ is hydrogen or methyl,
A is —$(CH_2)_n$—, wherein n is 0 or an integer from 1 to 7, or >N—CO—$R_5$, wherein $R_5$ is alkyl of 1 to 16 carbon atoms, alkenyl of 3 to 6 carbon atoms, cycloalkyl of 3 to 8 carbon atoms, 1-adamantyl, or —$(CH_2)_m$—$R_6$, wherein
m is 0 or an integer from 1 to 4, and
$R_6$ is phenyl; phenyl monosubstituted by fluorine, chlorine, bromine, alkyl or alkoxy of 1 to 4 carbon atoms, alkylmercapto of 1 to 4 carbon atoms, or phenyl; phenyl substituted by two or three substitutents of the group chlorine, alkyl or alkoxy of 1 to 4 carbon atoms; diphenylmethyl, the phenyl rings of which may be monosubstituted by fluorine, chlorine, bromine, alkyl or alkoxy of 1 to 4 carbon atoms; or naphthyl, or —$OR_7$, wherein
$R_7$ is alkyl of 1 to 4 carbon atoms, or alkenyl of 2 to 4 carbon atoms or phenyl or phenalkyl, which may be monosubstituted on the phenyl ring by chlorine, alkyl or alkoxy of 1 to 4 carbon atoms, and in which the alkylene chain of phenylalkyl is of 1 to 4 carbon atoms,
$R_8$ and $R_9$ are each hydrogen or alkyl of 1 to 4 carbon atoms,
or a pharmaceutically acceptable acid addition salt thereof are useful in the treatment of hypertension.

17 Claims, No Drawings

3-HYDRAZINO CYCLOALKYL[C]PYRIDAZINES AS ANTIHYPERTENSIVE AGENTS

This is a continuation of application Ser. No. 640,633, filed Dec. 15, 1975, now abandoned, which in turn is a continuation of application Ser. No. 485,578, filed July 3, 1974, now U.S. Pat. No. 3,954,754, which in turn is a continuation-in-part of Ser. No. 251,035, filed May 8, 1972, now U.S. Pat. No. 3,838,125, issued Sept. 4, 1976.

This invention relates to aminopyridazine derivatives.

In accordance with the invention there are provided new compounds of formula I,

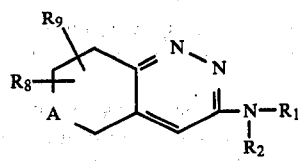
I wherein
$R_1$ is amino, or an

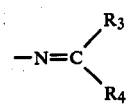

group, wherein each of
$R_3$ and $R_4$ is alkyl of 1 to 4 carbon atoms, or
$R_3$ and $R_4$ together with the carbon atom to which they are bound, form a cycloalkylidene radical of 5 to 12 carbon atoms,
$R_2$ is hydrogen or methyl,
A is a $-(CH_2)_n-$ group, wherein
n is 0 or an integer from 1 to 7, or an $>N-CO-R_5$ group, wherein
$R_5$ is alkyl or alkenyl of 1 to 16 carbon atoms, cycloalkyl of 3 to 8 carbon atoms, 1-adamantyl, or a $-(CH_2)_m-R_6$ group, wherein
m is 0 or an integer from 1 to 4, and
$R_6$ is phenyl; phenyl monosubstituted by fluorine, chlorine, bromine, alkyl or alkoxy of 1 to 4 carbon atoms, alkylmercapto of 1 to 4 carbon atoms, or phenyl; phenyl substituted by two or three substituents of the group chlorine, alkyl or alkoxy of 1 to 4 carbon atoms; diphenylmethyl, the phenyl rings of which may be monosubstituted by fluorine, chlorine, bromine, alkyl or alkoxy of 1 to 4 carbon atoms; or naphthyl, or an $-OR_7$ group, wherein
$R_7$ is alkyl or alkenyl of 1 to 4 carbon atoms, or phenyl, phenylalkyl or phenylalkenyl which may be monosubstituted on the phenyl ring by chlorine, alkyl or alkoxy of 1 to 4 carbon atoms, and in which the alkylene or alkenylene chain is of 1 to 4 carbon atoms,
and $R_8$ and $R_9$ are each hydrogen or alkyl of 1 to 4 carbon atoms,
and acid addition salts thereof.

Further, in accordance with the invention a compound of formula I or an acid addition salt thereof may be obtained by processes which comprise
(a) reacting a compound of formula IIa,

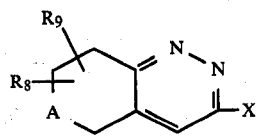
IIa wherein
$R_8$, $R_9$ and A are as defined above, and
X is chlorine, bromine, mercapto, or an $-SR_{10}$ group, wherein $R_{10}$ is benzyl or alkyl of 1 to 4 carbon atoms,
with a compound of formula III,

III wherein $R_2$ is as defined above, to produce a compound of formula Ia,

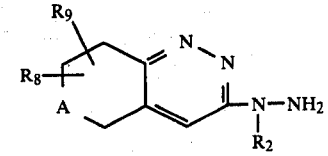
Ia wherein $R_2$, $R_8$, $R_9$ and A are as defined above, or
(b) reacting a compound of formula Ia with a compound of formula IV,

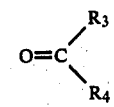
IV wherein $R_3$ and $R_4$ are as defined above, to produce a compound of formula Ib,

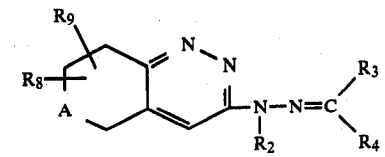
Ib wherein $R_2$, $R_3$, $R_4$, $R_8$, $R_9$ and A are as defined above, and, where an acid addition salt is required, converting the resulting compound of formula I into such salt.

When $R_1$ is N-alkylidene, the alkyl radicals $R_3$ and $R_4$ therein are preferably methyl or ethyl groups. When $R_1$ is N-cycloalkylidene, this preferably contains 5 or 6 carbon atoms.

When A denotes an alkylene chain, this is preferably of 2 or 3 carbon atoms and is especially propylene.

When $R_8$ and $R_9$ are alkyl radicals, these especially signify methyl or tert.butyl.

When $R_5$ is alkyl or alkenyl, the alkyl radicals preferably contain 1 to 7, especially 2 to 4 carbon atoms, and the alkenyl radicals preferably contain 3 to 6, especially 3 carbon atoms. When $R_5$ is cycloalkyl, it is preferably of 4 to 6 carbon atoms.

When $R_5$ is phenylalkyl, the alkylene chain thereof preferably contains 1 to 3, especially 1 carbon atom. $R_5$ preferably, however, is an $-OR_7$ radical, or a phenylor diphenyl radical which may be substituted and is especially a phenyl radical which may be substituted. When a phenyl group in the substituent $R_5$ is substituted by an alkyl or alkoxy radical, these radicals preferably contain 1 or 2 carbon atoms.

When $R_7$ is an alkyl or alkenyl radical, this preferably contains 2 or 3 carbon atoms. When $R_7$ is phenylalkyl, the alkylene chain thereof preferably contains 1 to 3 carbon atoms. When a phenyl ring in the substituent $R_7$ is substituted by an alkyl or alkoxy radical, these radicals preferably contain 1 or 2 carbon atoms.

Process variant (a) is preferably effected by reacting a compound of formula IIa either with an excess of a compound of formula III, e.g. 5 to 10 mols of a compound of formula III per mol of a compound of formula IIa, or in the presence of another basic agent capable of binding an acid which may result during the reaction, e.g. a tertiary amine, or an alkali metal or alkaline earth metal hydroxide or carbonate. The reaction may be effected in the presence of an inert, preferably polar, organic solvent, e.g. a lower alcohol such as methanol, ethanol or isopropanol, or an open chain or cyclic ether such as dioxane, diethylene glycol dimethyl ether or tetrahydrofuran. An excess of a compound of formula III may also be used as solvent.

When a compound of formula IIb,

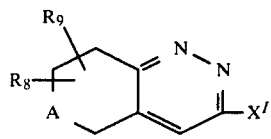

wherein $R_8$, $R_9$ and A are as defined above, and $X^I$ is chlorine, bromine or mercapto, is used, the reaction may, for example, be effected by heating a compound of formula IIb in hydrazine hydrate or methylhydrazine, optionally with the addition of one of the solvents and/or basic condensation agents indicated above, at normal pressure, at a temperature from approximately 20° to approximately 150° C., preferably at a temperature from 80° to 120° C., or at the boiling temperature of the reaction mixture, and under such conditions the reaction time is from 1 to 20 hours.

When a compound of formula IIc,

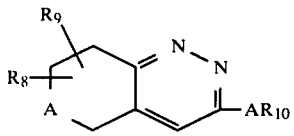

wherein $R_8$, $R_9$, $R_{10}$ and A are as defined above, is used, the reaction is preferably effected with an excess of hydrazine hydrate or methylhydrazine, optionally with the addition of one of the solvents and/or basic condensation agents indicated above, in an autoclave, at a temperature from 80° to 150° C.

Process variant (b) is preferably effected in the presence of an inert, preferably polar organic solvent, e.g. a lower alcohol such as methanol, ethanol or isopropanol, or an open chain or cyclic ether, e.g. diethylene glycol dimethyl ether, tetrahydrofuran or dioxane. Suitable reaction temperatures are from approximately 0° C. to the boiling temperature. Reaction times under preferred conditions are about 5 minutes to 20 hours. The product may be isolated by evaporating the reaction mixture to dryness, or allowing the crude product to crystallize as such or after extensive concentration of the solution.

The resulting compounds of formula I may be isolated from the reaction mixture and purified in accordance with known methods; the free bases may be converted into acid addition salts, and acid addition salts into free bases in conventional manner.

The starting materials may be obtained as follows:

(i) A compound of formula IId,

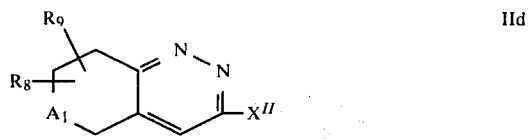

wherein $A_1$ is a $—(CH_2)_n—$ group, wherein n is as defined above, the imino group, or an $>N—COOR_7^I$ group, wherein $R_7^I$ is alkyl of 1 to 4 carbon atoms, or phenyl or phenylalkyl which may be monosubstituted on the phenyl ring by chlorine, alkyl or alkoxy of 1 to 4 carbon atoms, and in which the alkylene chain is of 1 to 4 carbon atoms, $R_8$ and $R_9$ are as defined above, and $X^{II}$ is chlorine or bromine, may be obtained by heating a compound of formula IIe,

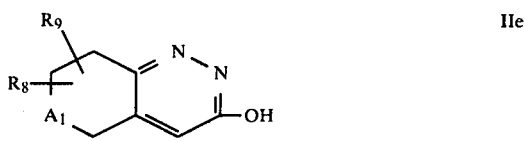

wherein $A_1$, $R_8$ and $R_9$ are as defined above, with a suitable chlorinating or brominating agent, e.g. phosphorus oxychloride, phosphorus tri- or pentachloride, or phosphorus oxybromide, preferably to a temperature up to approximately 100° C. or to the boiling temperature of the reaction mixture.

(ii) A compound of formula IIf,

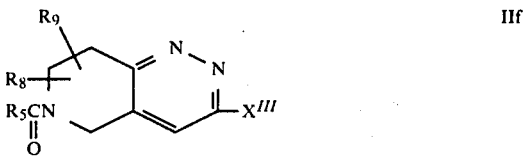

wherein $R_5$, $R_6$ and $R_9$ are as defined above, and $X^{III}$ is chlorine, bromine, hydroxy or mercapto, may be obtained by reacting a compound of formula IIg,

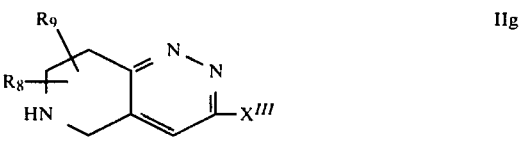

wherein $R_8$, $R_9$ and $X^{III}$ are as defined above, with a compound of formula V, $$R_5—CO—Cl \qquad V$$

wherein $R_5$ is as defined above, in an inert solvent, e.g. a chlorinated hydrocarbon such as chloroform or ethylene chloride, in the presence of an acid-binding agent, e.g. an alkali metal carbonate or a tertiary amine such as triethyl amine, and where $X^{III}$ is hydroxy or mercapto, the phenol or thiophenol ester resulting as by-product is saponified under weakly alkaline or acid conditions.

(iii) A compound of formula IIh,

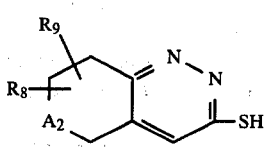

IIh wherein
$R_8$ and $R_9$ are as defined above, and
$A_2$ denotes A or imino,
may, for example, be obtained by reacting a compound of formula IIi,

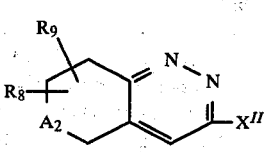

IIi wherein $R_8$, $R_9$, $A_2$ and $X^{II}$ are as defined above, with thiourea or, if desired, with sodium sulphide. The reaction is preferably effected in a polar organic solvent, e.g. a lower alcohol such as ethanol or dimethyl formamide, at a temperature from approximately 30° to approximately 100° C. Suitable reaction times are approximately ½ to 4 hours.

(iv) A compound of formula IIc may, for example, be obtained by reacting a compound of formula IIj,

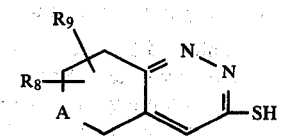

IIj wherein $R_8$, $R_9$ and A are as defined above, with a compound of formula VI,

(VI)

wherein $R_{10}$ and $X^{II}$ are as defined above, in the presence of an acid-binding agent, e.g. an alkaline earth carbonate or an alkali carbonate or hydroxide, e.g. potassium carbonate. The reaction is preferably effected in a polar organic solvent having a good dissolving power for the compound of formula IIj, e.g. in dimethyl formamide.

(v) A compound of formula IIk,

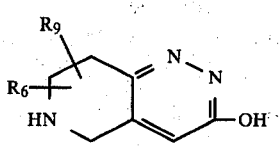

IIk wherein $R_8$ and $R_9$ are as defined above, may, for example, be produced by splitting off the $R_7{}^I$O—CO— group in a compound of formula III,

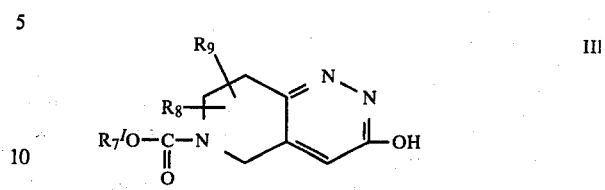

III wherein $R_7{}^I$, $R_8$ and $R_9$ are as defined above, with an acid, e.g. by heating for several hours in the acid medium, e.g. in hydrochloric acid, or with an alkali, e.g. by heating with an alkali metal hydroxide such as potassium hydroxide in a higher boiling alkanol such as n-butanol.

(vi) A compound of formula IIm,

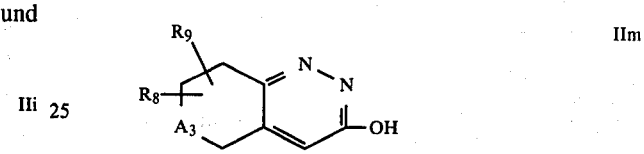

IIm wherein
$R_8$ and $R_9$ are as defined above, and
$A_3$ is a —(CH$_2$)$_n$— group, wherein n is as defined above, or an >N—COOR$_7{}^I$ group, wherein $R_7{}^I$ is as defined above,
may, for example, be obtained by cyclizing a compound of formula VII,

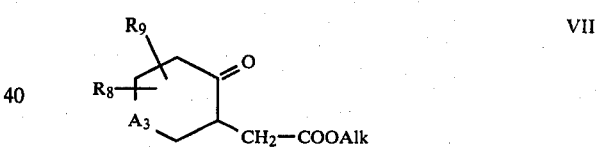

VII wherein
$A_3$, $R_8$ and $R_9$ are as defined above, and
Alk is alkyl of 1 to 4 carbon atoms,
in an inert solvent, e.g. a lower alcohol such as ethanol, in the presence of at least an equivalent amount of glacial acetic acid, with hydrazine hydrate or a salt of hydrazine. Suitable reaction temperatures are from 70° to 110° C., preferably the boiling temperature of the reaction mixture. The reaction may conveniently be effected under an inert gas atmosphere.

The resulting compound of formula VIII,

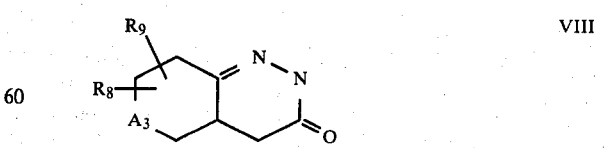

VIII wherein $A_3$, $R_8$ and $R_9$ are as defined above, is oxidized, preferably with bromine, using a halogenated hydrocarbon such as chloroform or ethylene chloride as solvent.

A compound of formula VII may be obtained by reacting a compound of formula IX,

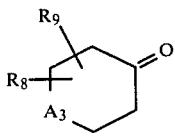

wherein $A_3$, $R_8$ and $R_9$ are as defined above, with a secondary amine, preferably a cyclic amine such as pyrrolidine, morpholine or piperidine, preferably in an inert organic solvent, e.g. an aromatic hydrocarbon such as benzene, if desired with the addition of a catalyst, e.g. p-toluenesulphonic acid or a molecular sieve, at an elevated temperature, preferably at the boiling temperature of the reaction mixture, to obtain an enamine of formula X,

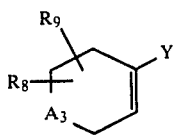

wherein
$A_3$, $R_8$ and $R_9$ are as defined above, and
Y is a secondary amino group,
and adding to this enamine, at room temperature, a bromoacetic acid alkyl ester in the presence of an inert organic solvent, e.g. an aromatic hydrocarbon such as benzene, a hydrocarbon halide such as chloroform, or an ether, or dimethyl formamide, heating the reaction mixture for several hours, preferably to the boil, and again splitting the enamine group in the resulting reaction product of formula XI,

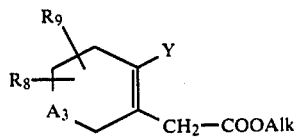

wherein
$A_3$, $R_8$, $R_9$ and Y are as defined above, and
Alk is alkyl of 1 to 4 carbon atoms,
by heating with water, if desired with the addition of a dilute lye, ammonia solution or dilute mineral acid.

Insofar as the production of the starting materials is not particularly described, these are known or may be produced in accordance with known processes, or in a manner analogous to the processes described herein or to known processes.

The compounds of formula I are useful because they possess pharmacological activity in animals. In particular, the compounds are useful as antihypertensive agents as indicated by tests in the hypertonic Grollman rat [method in accordance with A. Grollman, Proc. Soc. Exp. Biol. Med. 57, 104 (1914)] on administration of 0.1 to 10 mg/kg animal body weight of the compound.

For the above mentioned use, the dosage administered will, of course, vary depending upon the compound employed, mode of administration and treatment desired. However, in general, satisfactory results are obtained when administered at a daily dosage of from about 0.1 to 10 mg/kg animal body weight, preferably given in divided doses 2 to 4 times a day, or in sustained release form. For the larger mammals, the total daily dosage is in the range of from about 5 to 700 mg, and dosage forms suitable for oral administration comprise from about 1.3 to 350 mg of the compound admixed with a solid or liquid carrier or diluent.

Particularly interesting compounds are 6-benzoyl-3-hydrazino-5,6,7,8-tetrahydropyrido[4,3-c]pyridazine and the corresponding isopropylidene hydrazone derivative, 3-hydrazino-5,6,7,8-tetrahydro-6-pyride[4,3-c]pyridazinecarboxylic acid ethyl ester and the corresponding isopropylidene and 2-butylidene-hydrazone derivatives, and 3-hydrazino-5,6,7,8,9,10-hexahydrocycloocta[c] pyridazine and the corresponding isopropylidenehydrazone derivative.

The above compounds, when administered in a capsule containing from about 5 to 700 mg, produce the antihypertensive affect.

The compounds of formula I may be administered in pharmaceutically acceptable acid addition salt form. Such salt forms possess the same order of activity as the free bases and are readily prepared in conventional manner. Suitable such salt forms include organic acid salts such as the fumarate, tartrate and benzene-sulphonate, and mineral acid salts such as the hydrochloride, hydrobromide and sulphate.

The invention also provides a pharmaceutical composition comprising a compound of formula I, in free base or pharmaceutically acceptable acid addition salt form, in association with a pharmaceutical carrier or diluent. A suitable pharmaceutical form is a tablet, dragee, or capsule.

The invention also provides a method of treating hypertension in a warm-blooded animal, which comprises administering to an animal in need of such treatment a therapeutically effective dose of a compound of formula I or a pharmaceutically acceptable acid addition salt thereof.

In the following non-limitative Examples all temperatures are indicated in degrees Centigrade.

EXAMPLE 1

3-Hydrazino-5,6,7,8-tetrahydrocinnoline

A mixture of 20.2 g of 3-chloro-5,6,7,8-tetrahydrocinnoline and 100 cc of hydrazine hydrate in 50 cc of absolute ethanol is heated at a bath temperature of 110° for 17½ hours while stirring. After cooling the reaction mixture, this is almost completely concentrated, whereupon the title compound crystallizes as free base upon cooling with ice. M.P. 134°–138° from dimethoxyethane/ether.

5.5 g of the title compound are boiled in 150 cc of absolute ethanol with 7 g of fumaric acid. After filtration and cooling of the reaction mixture, the yellow 3-hydrazino-5,6,7,8-tetrahydrocinnoline fumarate crystallizes. M.P. 158°–161° (decomp.).

EXAMPLE 2

3-Hydrazino-5,6,7,8,9,10-hexahydrocycloocta[c-]pyridazine 11.7 g of 3-chloro-5,6,7,8,9,10-hexahydrocycloocta[c-]pyridazine and 60 cc of hydrazine hydrate are reacted in accordance with the process described in Example 1. The orange-coloured solution is completely concentrated, and the remaining crystalline crude title compound is washed with water. M.P. 145°–145° (decomp., from absolute ethanol).

EXAMPLE 3

5,6,7,8,9,10-Hexahydro-3-(1-methylhydrazino)cycloocta[c]pyridazine

A suspension of 9.8 g of 3-chloro-5,6,7,8,9,10-hexahydrocycloocta[c]pyridazine in 50 cc of methylhydrazine is stirred in an oil bath of 45° for 24 hours. The material dissolves completely during heating. After the reaction is complete, the mixture is evaporated to dryness, and the crude crystalline title compound is recrystallized twice from ether. The title compound has a
M.P. of 78°–79° (decomp.).

EXAMPLE 4

3-Hydrazino-5,6,7,8-tetrahydro-6-methylcinnoline

A suspension of 9.1 g of 3-chloro-5,6,7,8-tetrahydro-6-methylcinnoline in 100 cc of hydrazine hydrate is vigorously stirred in an oil bath of 110° for 6 hours. The starting material melts upon heating and forms an oily pool. After cooling with ice, crude 3-hydrazino-5,6,7,8-tetrahydro-6-methylcinnoline precipitates. It is dissolved in chloroform, the solution is dried with sodium sulphate and concentrated in a vacuum. 9 g of the crude base are dissolved with 5.8 g of fumaric acid in 50 cc of methanol in a water bath. After cooling with ice, the bis(3-hydrazino-5,6,7,8-tetrahydro-6-methylcinnoline)-trisfumarate, having a
M.P. of 156°–158° (decomp.), crystallizes.

The starting material may be produced as follows:

(a) A mixture of 112.1 g of 4-methylcyclohexanone and 106.7 g of pyrrolidine in 1.0 liter of benzene is heated to the boil at reflux for 2 hours, and the resulting water is continuously removed azeotropically. The mixture is concentrated, and the crude 4-methyl-1-pyrrolidinylcyclohexene(1) obtained as yellow oil is used in the next stage.

(b) A mixture of 171.2 g of 4-methyl-1-pyrrolidinylcyclohexene(1) and 200.4 g of bromoacetic acid ethyl ester in 1.5 liters of benzene is heated at reflux while stirring for 20 hours. 750 cc of water are added to the mixture, and this is again heated to the boil at reflux for 3 hours, whereby 250 cc of a 10% aqueous ammonia solution are added after one hour. The organic phase is separated, dried over sodium sulphate and concentrated in a vacuum. The crude 4-methylcyclohexanone-2-acetic acid ethyl ester is used as such in the next stage.

(c) 200.1 g of crude 4-methylcyclohexanone-2-acetic acid ethyl ester and 50 g of hydrazine hydrate are stirred at reflux in 600 cc of absolute ethanol and 100 cc of glacial acetic acid in a stream of nitrogen for 5 hours. The dark solution is completely concentrated in a vacuum and subsequently divided between chloroform and a 10% aqueous caustic soda solution. After concentrating the organic phase in a vacuum, crude 2,3,4,4a,5,6,7,8-octahydro-6-methyl-3-cinnolinone is obtained as an oil, which crystallizes upon adding 1.2 liters of ether. M.P. 116°–118° from ethyl acetate.

(d) A mixture of 35.6 g of bromine in 75 cc of chloroform is added dropwise to a boiling solution of 39 g of 2,3,4,4a,5,6,7,8-octahydro-6-methyl-3-cinnolinone in 200 cc of chloroform within one hour, and the mixture is stirred for a further hour at the same temperature. The hydrobromide of the reaction product, resulting after cooling with ice, is taken up in 150 cc of a concentrated aqueous ammonia solution, and after a short time of action, insoluble 5,6,7,8-tetrahydro-3-hydroxy-6-methylcinnoline is filtered off. M.P. 193°–195° (decomp., from acetonitrile).

(e) 27.5 g of 5,6,7,8-tetrahydro-3-hydroxy-6-methylcinnoline are suspended in 120 cc of phosphorus oxychloride, and the suspension is heated to the boil while stirring. The resulting solution is stirred for 1 hour at the boil and then concentrated to an oil in a vacuum. 150 cc of ice/water and 40 cc of concentrated ammonia solution are added to this oil, and the mixture is extracted twice with a total of 300 cc of chloroform. The chloroform phase is concentrated in a vacuum, and 3-chloro-5,6,7,8-tetrahydro-6-methylcinnoline is dissolved out of the resulting semicrystalline oil with n-hexane while heating.
M.P. 65°–67° (decomp.).

EXAMPLE 5

3-Hydrazino-6,7,8,9-tetrahydro(5H)cyclohepta[c]pyridazine

A suspension of 13.7 g of 3-chloro-6,7,8,9-tetrahydro(5H)cyclohepta[c]pyridazine in 100 cc of hydrazine hydrate is stirred in an oil bath of 90° for 12 hours, whereby 30 cc of dioxane are added after 2½ hours. The mixture is concentrated to a red oil, this is taken up in 300 cc of chloroform, a small amount of a second layer is separated, and the chloroform solution is concentrated in a vacuum. The semicrystalline residue is immediately converted into the crystalline dihydrochloride of the title compound with hydrochloric acid in isopropanol. M.P. 225°–228° (decomp., from 95% ethanol).

The starting material may be produced as follows:

(a) 1-Pyrrolidinylcycloheptene(1): Produced in a manner analogous to that described in Example 4(a) from 112.2 g of cycloheptanone and 106.7 g of pyrrolidine in 300 cc of benzene and 2 g of p-toluenesulphonic acid. Reaction time 96 hours. The oily crude product is used for the next reaction without purification.

(b) Cycloheptanone-2-acetic acid ethyl ester: Produced in a manner analogous to that described in Example 4(b) from 291.5 g of crude 1-pyrrolidinylcycloheptene(1) and 400.4 g of bromoacetic acid ethyl ester. Reaction time 24 hours. The crude product is purified by distillation in a water pump vacuum.
B.P. 143°–159° at 14 mm of Hg.

(c) 2,3,4,4a,6,7,8,9-Octahydro(5H)cyclohepta[c]pyridazinone(3): Produced in a manner analogous to that described in Example 4(c) from 49.5 g of cycloheptanone-2-acetic acid ethyl ester and 12.5 g of hydrazine hydrate. Reaction time 4 hours. The yellow solution is concentrated in a vacuum, and the resulting oily crude product is crystallized from 200 cc of ether.
M.P. 108°–109° from 95% ethanol.

(d) 6,7,8,9-Tetrahydro(5H)-3-hydroxycyclohepta[c]pyridazine: Produced in a manner analogous to that described in Example 4(d) from 27.1 g of 2,3,4,4a,6,7,8,9-octahydro(5H)cyclohepta[c]pyridazinone(3) and 26.1 g of bromine M.P. 200°–203° (decomp., from 95% ethanol).

(e) 3-Chloro-6,7,8,9-tetrahydro(5H)cyclohepta[c]pyridazine: Produced in a manner analogous to that described in Example 4(e) from 21.6 g of 6,7,8,9-tetrahydro(5H)-3-hydroxycyclohepta[c]pyridazine and 120 cc of phosphorus oxychloride. M.P. 74°–75° (decomp., from n-hexane).

EXAMPLE 6

6-tert.Butyl-3-hydrazino-5,6,7,8-tetrahydrocinnoline

A suspension of 13.8 g of 6-tert.butyl-3-chloro-5,6,7,8-tetrahydrocinnoline in 100 cc of hydrazine hydrate is stirred in an oil bath of 100° for 23 hours, whereby 20 cc of tetrahydrofuran are added after 1 hour. The mixture is worked up as described in Example 4, and the resulting crude oily title compound is dissolved in 40 cc of absolute ethanol, and hydrochloric acid in ethanol is added to the solution until an acid reaction is obtained. The hydrochloride which crystallizes is triturated with 100 cc of concentrated ammonia, the insoluble title compound is filtered off and has a M.P. of 72°–73° (decomp.).

The starting material may be produced as follows:

(a) 4-tert.Butyl-1-pyrrolidinyl-cyclohexene(1): Produced in a manner analogous to that described in Example 4(a) from 154.2 g of 4-tert.butylcyclohexanone and 106.5 g of pyrrolidine. The crude compound obtained as yellow oil is used for the next reaction without purification.

(b) 4-tert.Butylcyclohexanone-2-acetic acid ethyl ester: Produced in a manner analogous to that described in Example 4(b) from 232 g of crude 4-tert.butyl-1-pyrrolidinylcyclohexene(1) and 200.4 g of bromoacetic acid ethyl ester. The crude compound is used for the next reaction without purification.

(c) 4-tert.Butyl-2,3,4,4a,5,6,7,8-octahydro-3-cinnolinone: Produced in a manner analogous to that described in Example 4(c) from 251.2 g of crude 4-tert.Butylcyclohexanone-2-acetic acid ethyl ester and 50 g of hydrazine hydrate. M.P. 161°–164° (decomp., from acetonitrile).

(d) 4-tert.Butyl-5,6,7,8-tetrahydro-3-hydrocinnoline: Produced in a manner analogous to that described in Example 4(d) from 31.7 g of 4-tert.butyl-2,3,4,4a,5,6,7,8-octahydro-3-cinnolinone and 24 g of bromine. Reaction time 90 minutes.

M.P. 220°–223° (decomp., from acetonitrile).

(d) 6-tert.Butyl-3-chloro-5,6,7,8-tetrahydrocinnoline: Produced in a manner analogous to that described in Example 4(e) from 14.1 g of 4-tert.-butyl-5,6,7,8-tetrahydro-3-hydroxycinnoline and 125 cc of phosphorus oxychloride.

M.P. 96°–97° (decomp., from n-hexane).

EXAMPLE 7

3-Hydrazino-5,6,7,8,9,10,11,12,13,14-decahydrocyclododeca[c]pyridazine 9.9 g of 3-chloro-5,6,7,8,9,10,11,12,13,14-decahydrocyclododeca[c]pyridazine and 200 cc of hydrazine hydrate are heated in an autoclave in an oil bath of 130° for 16½ hours. The reaction solution is cooled with ice/common salt, and the resulting crude product is boiled for a short time with 4 g of fumaric acid in 150 cc of isopropanol. The crystalline fumarate of the title compound is obtained upon cooling.

M.P. 173°–174° (decomp., from 95% ethanol).

The starting material may be produced as follows:

(a) 1-Pyrrolidinylcyclododecene(1): Produced in a manner analogous to that described in Example 4(a) from 364 g of cyclododecanone and 216 g of pyrrolidine in 2.8 liters of benzene with the addition of 6 g of p-toluenesulphonic acid. Reaction time 24 hours at the boil. The reaction mixture is concentrated to a yellow oil, and the unchanged starting material is separated in a water pump vacuum. The resulting crude product is used for the next reaction without purification.

(b) Cyclododecanone-2-acetic acid ethyl ester: Produced in a manner analogous to that described in Example 4(b) from 162.3 g of crude 1-pyrrolidinylcyclododecene(1) and 139 g of bromoacetic acid ethyl ester. Reaction time 17 hours. The crude product is used for the next reaction without purification.

(c) 2,3,4,4a,5,6,7,8,9,10,11,12,13,14-Tetradecahydrocyclododeca[c]pyridazinone(3): Produced in a manner analogous to that described in Example 4(c) from 205 g of crude cyclododecanone-2-acetic acid ethyl ester and 35 g of hydrazine hydrate. The mixture is allowed to stand over night at room temperature, is cooled with ice, and the resulting crude product is used for the next reaction as such.

(d) 5,6,7,8,9,10,11,12,13,14-Decahydro-3-hydroxycyclododeca[c]pyridazine: Produced in a manner analogous to that described in Example 4(d) from 60 g of 2,3,4,4a,5,6,7,8,9,10,11,12,13,14-tetradecahydrocyclododeca[c]pyridazinone(3) and 40.6 g of bromine.

M.P. 188°–189° (decomp., from isopropanol). The hydrobromide has a M.P. of 195°–198° from ethanol/ether.

(e) 3-Chloro-5,6,7,8,9,10,11,12,13,14-decahydrocyclododeca[c]pyridazine: Produced in a manner analogous to that described in Example 4(e) from 26 g of 5,6,7,8,9,10,11,12,13,14,15-decahydro-3-hydroxycyclododeca[c]pyridazine and 100 cc of phosphorus oxychloride. M.P. 126°–128° (decomp., from isopropanol).

EXAMPLE 8

6-Benzoyl-3-hydrazino-5,6,7,8-tetrahydropyrido[4,3-c]pyridazine

A suspension of 21.6 g of 6-benzoyl-3-chloro-5,6,7,8-tetrahydropyrido[4,3-c]pyridazine in 80 cc of hydrazine hydrate is boiled at reflux at an oil bath temperature of 110° for 1 hour. After a reaction time of approximately 15 minutes the material dissolves completely. The crude title compound resulting after cooling the mixture, is washed with a small amount of absolute ethanol and dissolved in 60 cc of dimethyl formamide. 60 cc of absolute ethanol are added to the solution, whereupon the title compound crystallizes.

M.P. 220°–223° (decomp.).

The starting material may be produced as follows:

(a) 1,2,3,6-Tetrahydro-4-pyrrolidinylpyridine-1-carboxylic acid ethyl ester: Produced in a manner analogous to that described in Example 4(a) from 342.6 g of 1-carbethoxy-4-piperidone and 214.0 g of pyrrolidine. The product is purified by distillation in a high vacuum. B.P. 144°–150° at 0.03 mm of Hg.

(b) 1-Carbethoxy-4-piperidone-3-acetic acid ethyl ester: Produced in a manner analogous to that described in Example 4(b) from 1460 g of 1,2,3,6-tetrahydro-4-pyrrolidinylpyridine-1-carboxylic acid ethyl ester and 1250 g of bromoacetic acid ethyl ester. The crude product is purified by vacuum distillation. B.P. 145°–170° at 0.05 mm of Hg.

(c) 2,3,4,4a,5,6,7,8-Octahydro-3-oxo-6-pyrido[4,3-c]pyridazinecarboxylic acid ethyl ester: Produced in a manner analogous to that described in Example 4(c) from 514 g of 1-carbethoxy-4-piperidine-3-acetic acid ethyl ester and 100 g of hydrazine hydrate. The crystalline crude product obtained after concentration of the mixture is recrystallized from 1 liter of 95% ethanol. M.P. 163°–166° (decomp.).

(d) 6-Carbethoxy-5,6,7,8-tetrahydro-3(2H)pyrido[4,3-c]pyridazinone: Produced in a manner analogous to that described in Example 4(d) from 450.5 g of 2,3,4,4a,5,6,7,8-octahydro-3-oxo-6-pyrido[4,3-c]pyridazinocarboxylic acid ethyl ester and 320 g of bromine. 1 kg of ice/water is added to the mixture, the chloroform portion is separated, and the acid aqueous phase is again extracted with 500 cc of chloroform. The semicrystalline crude product obtained after concentrating the chloroform phase, is recrystallized with 250 cc of absolute ethanol.

M.P. 165°–163° (decomp.).

(e) A solution of 223.2 g of 6-carbethoxy-5,6,7,8-tetrahydro-3(2H)pyrido[4,3-c]pyridazinone in 1 liter of concentrated hydrochloric acid is heated to the boil at reflux for 22 hours while stirring. The mixture is concentrated in a vacuum, and the resulting crude crystalline hydrochloride of 5,6,7,8-tetrahydro-3(2H)pyrido[4,3-c]pyridazinone, having a M.P. of 307°–310° (decomp., from methanol), is suspended in 0.75 liters of methanol, and 0.4 liters of triethylamine are slowly added to the suspension. After stirring for 15 minutes and cooling the violet suspension, the crude base is obtained. 25 g of the crude base are recrystallized from 300 cc of methanol, mixed with 10 cc of concentrated ammonia and 40 cc of water, with the addition of a small amount of coal. 5,6,7,8-Tetrahydro-3(2H)pyrido[4,3-c]pyridazinone has a M.P. of 223°–225° (decomp.).

(f) 3-Chloro-5,6,7,8-tetrahydropyrido[4,3-c]pyridazine: Produced in a manner analogous to that described in Example 4(e) from 30.3 g of 5,6,7,8-tetrahydro-3(2H)pyrido[4,3-c]pyridazinone and 250 cc of phosphorus oxychloride. The crude unstable base is converted into the maleate for working up. This is effected by boiling 24.8 g of the base in 150 cc of methanol with 17.5 g of maleic acid. Upon cooling the solution, the crude maleate is obtained, which is recrystallized from methanol with the addition of a small amount of coal. 3-Chloro-5,6,7,8-tetrahydropyrido[4,3-c]pyridazine maleate has a M.P. of 162°–164° (decomp.).

(g) A mixture of 12.6 g of benzoyl chloride in 100 cc of ethylene chloride is added dropwise to a suspension of 25.6 g of 3-chloro-5,6,7,8-tetrahydropyrido[4,3-c]pyridazine maleate in 250 cc of ethylene chloride and 21.8 g of triethylamine within 18 minutes at room temperature while stirring. The mixture is stirred at room temperature for a further 14 hours, 200 cc of water are added, the organic phase is separated and concentrated to an oil in a vacuum. Upon adding ether/dimethoxyethane to this oil, crude 6-benzoyl-3-chloro-5,6,7,8-tetrahydropyrido[4,3-c]pyridazine is obtained. After recrystallization from absolute ethanol with the addition of a small amount of coal, the compound has a M.P. of 125°–127° (decomp.).

EXAMPLE 9

3-Hydrazino-5,6,7,8-tetrahydro-6-(o-toluoyl)-pyrido[4,3-c]pyridazine 13.0 g of 3-chloro-5,6,7,8-tetrahydro-6-(o-toluoyl)-pyrido[4,3-c]pyridazine and 100 cc of hydrazine hydrate are reacted as described in Example 4. Reaction time 2 hours. The bis[3-hydrazino-5,6,7,8-tetrahydro-6-(o-toluoyl)pyrido[4,3-c]pyridazine]trisfumarate has a M.P. of 98°–100° (decomp., from 95% ethanol).

The starting material may be produced as follows:
3-Chloro-5,6,7,8-tetrahydro-6-(o-toluoyl)pyrido[4,3-c]pyridazine: Produced in a manner analogous to that described in Example 8(g), from 28.5 g of 3-chloro-5,6,7,8-tetrahydropyrido[4,3-c]pyridazine maleate and 16.9 g of o-toluoyl chloride. Reaction time 24 hours.

M.P. 123°–126° (decomp., from 95% ethanol/ether).

EXAMPLE 10

6-Benzoyl-5,6,7,8-tetrahydro-3-(1-methylhydrazino)-pyrido[4,3-c]pyridazine 13.7 g of 6-benzoyl-3-chloro-5,6,7,8-tetrahydropyrido[4,3-c]pyridazine in 40 cc of methyl hydrazine are stirred at a bath temperature of 50° for 6½ hours. The oil resulting after concentrating the reaction solution is dissolved in 200 cc of chloroform, the solution is dried with sodium sulphate and again concentrated to an oil. This is boiled for a short time with 12.0 g of gentisic acid in 100 cc of methanol on a water bath. After concentrating the solution to approximately ⅔ of its volume, and cooling with ice, the bisgentisinate of the title compound precipitates.

M.P. 166°–168° (decomp., from absolute ethanol).

EXAMPLE 11

6-(o-Chlorobenzoyl)-3-hydrazino-5,6,7,8-tetrahydropyrido[4,3-c]pyridazine 7.7 g of 3-chloro-6-(o-chlorobenzoyl)-5,6,7,8-tetrahydropyrido[4,3-c]pyridazine and 30 cc of hydrazine hydrate are stirred at a bath temperature of 80° for 20 hours with the addition of 25 cc of isopropanol, and the mixture is worked up as described in Example 4. The light yellow foam, obtained after concentrating the chloroform phase, is dissolved in 50 cc of 95% ethanol and boiled for a short time on a water bath with 5.8 g of fumaric acid. The bis[6-(o-chlorobenzoyl)-3-hydrazino-5,6,7,8-tetrahydropyrido[4,3-c]pyridazine]trisfumarate has a M.P. of 144°–146° (decomp., from 95% ethanol).

The 3-chloro-6-(o-chlorobenzoyl-5,6,7,8-tetrahydropyrido[4,3-c]pyridazine, required as starting material, may be obtained in a manner analogous to that described in Example 8(g), from 28.5 g of 3-chloro-5,6,7,8-tetrahydropyrido[4,3-c]pyridazine maleate and 16.9 g of o-chlorobenzoyl chloride. M.P. 97°–99° (decomp., from 95% ethanol).

EXAMPLE 12

3-Hydrazino-5,6,7,8-tetrahydro-6-(3-phenylpropionyl)-pyrido[4,3-c]pyridazine 8.5 g of 3-chloro-5,6,7,8-tetrahydro-6-(3-phenylpropionyl)pyrido[4,3-c]pyridazine and 80 cc of hydrazine hydrate are stirred at a bath temperature of 80° for 4 hours. After cooling the reaction solution with ice, the title compound precipitates and is recrystallized from 95% ethanol. The title compound has a M.P. of 162°–165° (decomp.).

The 3-chloro-5,6,7,8-tetrahydro-6-(3-phenylpropionyl)pyrido[4,3-c]pyridazine, required as starting material, may be obtained in a manner analogous to that described in Example 8(g), from 28.6 g of 3-chloro-5,6,7,8-tetrahydropyrido[4,3-c]pyridazine maleate and 31.5 g of 3-phenylpropionyl chloride. M.P. 134°–137° from 95% ethanol.

EXAMPLE 13

6-(p-tert.Butylbenzoyl)-3-hydrazino-5,6,7,8-tetrahydropyrido[4,3-c]pyridazine 12.0 g of 6-(p-tert.-butylbenzoyl)-3-chloro-5,6,7,8-tetrahydropyrido[4,3-c]pyridazine and 75 cc of hydrazine hydrate are stirred at a bath temperature of 100° for 4 hours. The crude crystalline base obtained after cooling the mixture with ice, is dissolved together with 7.2 g of fumaric acid in 50 cc of methanol, whereby the bis[6-(p-tert.-butylbenzoyl)-3-hydrazine-5,6,7,8-tetrahydropyrido[4,3-c]pyridazine]trisfumarate is obtained. M.P. 115°-118° (decomp.).

The 6-(p-tert.-butylbenzoyl)-3-chloro-5,6,7,8-tetrahydropyrido[4,3-c]pyridazine, required as starting material, may be obtained in a manner analogous to that described in Example 8(g), from 34.2 g of 3-chloro-5,6,7,8-tetrahydropyrido[4,3-c]pyridazine maleate and 25 g of tert.butylbenzoyl chloride. M.P. 157°-160° (decomp., from 95% ethanol).

EXAMPLE 14

6-(3,3-Diphenylpropionyl)-3-hydrazino-5,6,7,8-tetrahydropyride[4,3-c]pyridazine 7.6 g of 3-chloro-6-(3,3-diphenylpropionyl)-5,6,7,8-tetrahydropyrido[4,3-c]pyridazine in 40 cc of hydrazine hydrate and 40 cc of dioxane are stirred at a bath temperature of 100° during 12 hours. The mixture is cooled with ice, whereupon the title compound precipitates and is recrystallized from ethanol/water (ratio 6:1). The title compound has a M.P. of 208°-211° (decomp.).

The 3-chloro-6-(3,3-diphenylpropionyl)-5,6,7,8-tetrahydropyrido[4,3-c]pyridazine, required as starting material, may be obtained in a manner analogous to that described in Example 8(g), from 14.3 g of 3-chloro-5,6,7,8-tetrahydropyrido[4,3-c]pyridazine maleate and 12.3 g of β,β-diphenylpropionic acid chloride. Reaction time 24 hours. The oily crude product is taken up in 100 cc of absolute ethanol, whereupon it crystallizes. M.P. 175°-178° (decomp., from methanol).

EXAMPLE 15

6-(3,4-Dichlorobenzoyl)-3-hydrazino-5,6,7,8-tetrahydropyrido[4,3c]pyridazine 10.2 g of 3-chloro-6-(3,4-dichlorobenzoyl)-5,6,7,8-tetrahydropyrido[4,3-c]pyridazine and 60 cc of hydrazine hydrate are stirred at a bath temperature of 80° for 24 hours. 50 cc of isopropanol are subsequently added, and the mixture is heated for a further 2 hours. The crude title compound precipitates upon cooling the mixture in an ice/methanol bath. It is triturated with 50 cc of a 10% aqueous caustic soda solution, and the insoluble material is filtered off and recrystallized from 95% ethanol. The title compound has a M.P. of 202°-206° (decomp.).

The 3-chloro-6-(3,4-dichlorobenzoyl)-5,6,7,8-tetrahydropyrido[4,3-c]pyridazine, required as starting material, may be obtained in a manner analogous to that described in Example 8(g), from 3-chloro-5,6,7,8-tetrahydropyrido[4,3-c]pyridazine maleate and 3,4-dichlorobenzoyl chloride. M.P. 188°-191° (decomp., from dimethyl formamide).

EXAMPLE 16

6-(2,6-Dischlorobenzoyl)-3-hydrazino-5,6,7,8-tetrahydropyrido[4,3-c]pyridazine 10.3 g of 3-chloro-6-(2,6-dichlorobenzoyl)-5,6,7,8-tetrahydropyrido[4,3-c]pyridazine and 30 cc of hydrazine hydrate are stirred at a bath temperature of 100° for 24 hours with the addition of 40 cc of dioxane, and the mixture is worked up as described in Example 13. The bis[6-(2,6-dichlorobenzoyl)-3-hydrazino-5,6,7,8-tetrahydropyrido[4,3-c]pyridazine]fumarate has a M.P. of 209°-211° (decomp., from absolute ethanol).

The 3-chloro-6-(2,6-dichlorobenzoyl)-5,6,7,8-tetrahydropyrido[4,3-c]pyridazine, required as starting material, may be produced from 3-chloro-5,6,7,8-tetrahydropyrido[4,3-c]pyridazine maleate and 2,6-dichlorobenzoyl chloride in a manner analogous to that described in Example 8(g). The oily crude product is taken up in absolute ethanol, whereby crystallization occurs. M.P. 181°-184° (decomp., from acetonitrile).

EXAMPLE 17

6-(2,3-Dimethylbenzoyl)-3-hydrazino-5,6,7,8-tetrahydropyrido[4,3-c]pyridazine 10.3 g of 3-chloro-6-(2,3-dimethylbenzoyl)-5,6,7,8-tetrahydropyrido[4,3-c]pyridazine and 50 cc of hydrazine hydrate in 80 cc of dioxane are heated in an oil bath of 80°. After a reaction time of 60 hours, the mixture is concentrated in a vacuum, the oily residue is divided between 250 cc of chloroform and 150 cc of water, and after concentrating the chloroform phase, the resulting oily crude base is reacted with gentisic acid as described in Example 10. The gentisinate of the title compound has a M.P. of 176°-179° (decomp.) after recrystallization from 150 cc of methanol and 100 cc of water.

The 3-chloro-6-(2,3-dimethylbenzoyl)-5,6,7,8-tetrahydropyrido[4,3-c]pyridazine, required as starting material, may be obtained in a manner analogous to that described in Example 8(g), from 3-chloro-5,6,7,8-tetrahydropyrido[4,3-c]pyridazine maleate and 2,3-dimethylbenzoyl chloride. Reaction time 64 hours. M.P. 189°-192° (decomp., from absolute ethanol).

EXAMPLE 18

3-Hydrazino-5,6,7,8-tetrahydro-6-(3,4,5-trimethoxybenzoyl)pyrido[4,3-c]pyridazine 12.8 g of 3-chloro-5,6,7,8-tetrahydro-6-(3,4,5-trimethoxybenzoyl)pyrido[4,3-c]pyridazine and 40 cc of hydrazine hydrate in 40 cc of dioxane are stirred at a bath temperature of 100° for 4½ hours. The title compound has a M.P. of 194°-197° (decomp., from absolute ethanol/methanol 2:1).

The 3-chloro-5,6,7,8-tetrahydro-6-(3,4,5-trimethoxybenzoyl)pyrido[4,3-c]pyridazine, required as starting material, may be produced in a manner analogous to that described in Example 8(g), from 3-chloro-5,6,7,8-tetrahydropyrido[4,3-c]pyridazine maleate and 3,4,5-trimethoxybenzoyl chloride. M.P. 165°-168° (decomp., from absolute ethanol).

EXAMPLE 19

3-Hydrazino-5,6,7,8-tetrahydro-6-(4-phenylbutyryl)-pyrido[4,3-c]pyridazine 11.8 g of 3-chloro-5,6,7,8-tetrahydro-6-(4-phenylbutyryl)pyrido[4,3-c]pyridazine and 60 cc of hydrazine hydrate are stirred at a bath temperature of 50° for 53 hours with the addition of 50 cc of dioxane. The mixture is worked up as described in Example 10. The qentisinate of the title compound has a M.P. of 203°-205° (decomp., from methanol/water 2:1).

The 3-chloro-5,6,7,8-tetrahydro-6-(4-phenylbutyryl)-pyrido[4,3-c]pyridazine, required as starting material, may be produced in a manner analogous to that described in Example 8(g), from 3-chloro-5,6,7,8-tetrahydropyrido[4,3-c]pyridazine maleate and phenylbutyric acid chloride. M.P. 92°-94° (decomp.).

EXAMPLE 20

3-Hydrazino-5,6,7,8-tetrahydro-6-(p-toluoyl)pyrido[4,3-c]pyridazine 12.0 g of 3-chloro-5,6,7,8-tetrahydro-6-(p-toluoyl)pyrido[4,3-c]pyridazine and 50 cc of hydrazine hydrate are stirred at a bath temperature of 100° for 2 hours. The title compound has a M.P. of 207°-210° (decomp., from 95% ethanol).

The 3-chloro-5,6,7,8-tetrahydro-6-(p-toluoyl)pyrido[4,3-c]pyridazine, required as starting material, may be produced in a manner analogous to that described in Example 8(g), from 3-chloro-5,6,7,8-tetrahydropyrido[4,3-c]pyridazine maleate and p-toluoyl chloride. Reaction time 24 hours at room temperature. M.P. 152°-153° (decomp., from absolute ethanol).

EXAMPLE 21

6-(m-Chlorobenzoyl)-3-hydrazino-5,6,7,8-tetrahydropyrido[4,3-c]pyridazine 10.8 g of 3-chloro-6-(m-chlorobenzoyl)-5,6,7,8-tetrahydropyrido[4,3-c]pyridazine and 50 cc of hydrazine hydrate are stirred at a bath temperature of 100° for 4 hours with the addition of 25 cc of isopropanol, and the mixture is worked up to a crude base as described in Example 17, and this crude base is converted into the fumarate in a manner analogous to that described in Example 4. The fumarate of the title compound has a M.P. of 178°-180° (decomp., from absolute ethanol).

The 6-(m-chlorobenzoyl)-3-chloro-5,6,7,8-tetrahydropyrido[4,3-c]pyridazine, required as starting material, is obtained in a manner analogous to that described in Example 8(g), from 3-chloro-5,6,7,8-tetrahydropyrido[4,3-c]pyridazine maleate and m-chlorobenzoyl chloride. M.P. 194°-197° (decomp., from methanol).

EXAMPLE 22

6-(p-Bromobenzoyl)-3-hydrazino-5,6,7,8-tetrahydropyrido[4,3-c]pyridazine 10.2 g of 6-(p-bromobenzoyl)-3-chloro-5,6,7,8-tetrahydropyrido[4,3-c]pyridazine and 55 cc of hydrazine hydrate are stirred at a bath temperature of 100° for 2 hours. The title compound has a M.P. of 192°-195° (decomp., from absolute ethanol/methanol 3:1).

The 6-(p-bromobenzoyl)-3-chloro-5,6,7,8-tetrahydropyrido[4,3-c]pyridazine, required as starting material, may be obtained in a manner analogous to that described in Example 8(g), from 3-chloro-5,6,7,8-tetrahydropyrido[4,3-c]pyridazine maleate and p-bromobenzoyl chloride. M.P. 164°-167° (decomp., from absolute ethanol).

EXAMPLE 23

3-Hydrazino-5,6,7,8-tetrahydro-6-(p-methoxybenzoyl)pyrido[4,3-c]pyridazine 10.5 g of 3-chloro-5,6,7,8-tetrahydro-6-(p-methoxybenzoyl)pyrido[4,3-c]pyridazine and 100 cc of hydrazine hydrate are stirred at a bath temperature of 100° for 1 hour. The title compound has a M.P. of 169°-172° (decomp., from 95% ethanol).

The 3-chloro-5,6,7,8-tetrahydro-6-(p-methoxybenzoyl)pyrido[4,3-c]pyridazine, required as starting material, may be obtained in a manner analogous to that described in Example 8(g), from 3-chloro-5,6,7,8-tetrahydropyrido[4,3-c]pyridazine maleate and p-methoxybenzoyl chloride. M.P. 163°-164° from 95% ethanol.

EXAMPLE 24

6-(o-Fluorobenzoyl)-3-hydrazino-5,6,7,8-tetrahydropyride[4,3-c]pyridazino 11.6 g of 3-chloro-6-(o-fluorobenzoyl)-5,6,7,8-tetrahydrepyrido[4,3-c]pyridazine and 80 cc of hydrazine hydrate are stirred at a bath temperature of 100° for 3½ hours. The title compound has a M.P. of 210°-213° (decomp., from 95% ethanol/methanol 1:1).

The 3-chloro-6-(o-fluorobenzoyl)-5,6,7,8-tetrahydropyrido[4,3-c]pyridazine, required as starting material, may be obtained in a manner analogous to that described in Example 8(g), from 3-chloro-5,6,7,8-tetrahydropyrido[4,3-c]pyridazine maleate and o-fluorobenzoyl chloride. M.P. 144°-146° (decomp., from 95% ethanol).

EXAMPLE 35

3-Hydrazino-5,6,7,8-tetrahydro-6-(o-methylphenacetyl)pyrido[4,3-c]pyridazine 10.0 g of 3-chloro-5,6,7,8-tetrahydro-6-(o-methylphenacetyl)pyrido[4,3-c]pyridazine and 35 cc of hydrazine hydrate are stirred at a bath temperature of 100° for 30 minutes. The title compound has a M.P. of 155°-157° (decomp., from absolute ethanol).

The 3-chloro-5,6,7,8-tetrahydro-6-(o-methylphenacetyl)pyrido[4,3-c]pyridazine, required as starting material, may be obtained in a manner analogous to that described in Example 8(g), from 3-chloro-5,6,7,8-tetrahydropyrido[4,3-c]pyridazine maleate and o-methylphenacetyl chloride. M.P. 125°-127° (decomp., from 95% ethanol).

EXAMPLE 26

6-(p-Ethoxybenzoyl)-3-hydrazino-5,6,7,8-tetrahydropyrido[4,3-c]pyridazine 11.1 g of 6-(p-ethoxybenzoyl)-3-chloro-5,6,7,8-tetrahydropyrido[4,3-c]pyridazine and 60 cc of hydrazine hydrate are stirred at a bath temperature of 100° for 1 hour and 40 minutes. The title compound has a M.P. of 171°-173° (decomp., from absolute ethanol).

The 6-(p-ethoxybenzoyl)-3-chloro-5,6,7,8-tetrahydropyrido[4,3-c]pyridazine, required as starting material, may be obtained in a manner analogous to that described in Example 8(g), from 3-chloro-5,6,7,8-tetrahydropyrido[4,3-c]pyridazine maleate and p-ethoxybenzoyl chloride. M.P. 146°-149° (decomp., from 95% ethanol).

EXAMPLE 27

3-Hydrazino-5,6,7,8-tetrahydro-6-(2-naphthoyl)pyrido[4,3-c]pyridazine 8 g of 3-chloro-5,6,7,8-tetrahydro-6-(2-naphthoyl)pyrido[4,3-c]pyridazine and 60 cc of hydrazine hydrate are stirred at a bath temperature of 100° for 2 hours. After approximately 1 hour and 30 minutes, a dissolution and reprecipitation is observed. After cooling with ice the solid material is filtered off and recrystallized from 200 cc of methanol. The title compound has a M.P. of 204°-207° (decomp.).

The 3-chloro-6-(2-naphthoyl)-5,6,7,8-tetrahydropyrido[4,3-c]pyridazine, required as starting material, is produced in a manner analogous to that described in Example 8(g), from 3-chloro-5,6,7,8-tetrahydropyrido[4,3-c]pyridazine maleate and 2-naphthoyl chloride. Reaction time 22 hours at room temperature. M.P. 167°–170°(decomp., from 95% ethanol).

EXAMPLE 28

3-Hydrazino-5,6,7,8-tetrahydro-6-pivaloylpyrido[4,3-c]pyridazine 11.4 g of 3-chloro-5,6,7,8-tetrahydro-6-pivaloyl-pyrido[4,3-c]pyridazine and 100 cc of hydrazine hydrate are boiled at reflux at a bath temperature of 110° for 1½ hours while stirring. The crude title compound is taken up in 100 cc of chloroform, is dried with sodium sulphate, the chloroform solution is again concentrated, and recrystallized from 20 cc of absolute ethanol. The title compound has a M.P. of 158°–160° (decomp.).

The 3-chloro-5,6,7,8-tetrahydro-6-pivaloyl-pyrido[4,3-c]pyridazine, required as starting material, is produced in a manner analogous to that described in Example 8(g), from 3-chloro-5,6,7,8-tetrahy-dropyrido[4,3-c]pyridazine maleate and pivalic acid chloride. Reaction time 24 hours at room temperature. M.P. 140°–142° (decomp., from ethanol).

EXAMPLE 29

3-Hydrazino-5,6,7,8-tetrahydro-6-myristinoyl-pyrido[4,3-c]pyridazine 11.0 g of 3-chloro-5,6,7,8-tetrahydro-6-myristinoyl-pyrido[4,3-c]pyridazine and 110 cc of hydrazine hydrate are stirred at reflux at a bath temperature of 80° for 26 hours with the addition of 10 cc of tetrahydrofuran, and the mixture is worked up as described in Example 28. The crystalline crude base still contains a by-product, which may be separated by producing the hydrochloride. This is effected by dissolving the crude base in 100 cc of hydrochloric acid in ethanol. After a short time the hydrochloride of the title compound crystallizes. M.P. 210°–213° (decomp., from ethanol).

The 3-chloro-5,6,7,8-tetrahydro-6-myristinoyl-pyrido[4,3-c]pyridazine, required as starting material, is produced in a manner analogous to that described in Example 8 (g), from 3-chloro-5,6,7,8-tetrahy-dropyrido[4,3-c]pyridazine maleate and myristic acid chloride. M.P. 86°–87°from ethanol.

EXAMPLE 30

6-Butyryl-3-hydrazino-5,6,7,8-tetrahydropyrido[4,3-c]pyridazine 8.4 g of 6-butyryl-3-chloro-5,6,7,8-tetrahy-dropyrido[4,3-c]pyridazine and 30 cc of hydrazine hydrate are stirred at a bath temperature of 100°for 45 minutes, and the mixture is worked up as described in Example 4. The bis(6-butyryl-3-hydrazino-5,6,7,8-tet-rahydropyrido[4,3-c]pyridazine)trisfumarate has a M.P. of 177°–179° (decomp., from 95% ethanol/methanol 5:2).

The 6-butyryl-3-chloro-5,6,7,8-tetrahydropyrido[4,3-c]pyridazine, required as starting material, may be produced in a manner analogous to that described in Example 8(g), from 3-chloro-5,6,7,8-tetrahydropyrido[4,3-c]pyridazine maleate and butyric acid chloride. Reaction time 27 hours. M.P. 130°–133° from acetonitrile.

EXAMPLE 31

3-Hydrazino-6-octanoyl-5,6,7,8-tetrahydropyrido[4,3-c]pyridazino 11.5 g of 3-chloro-6-octanoyl-5,6,7,8-tetrahy-dropyrido[4,3-c]pyridazine, dissolved in 50 cc of dioxane, and 30 cc of hydrazine hydrate are stirred at a bath temperature of 100° for 16 hours, and the mixture is worked up as descirbed in Example 17. The gentisinate of the title compound has a M.P. of 164°–166° (decomp., from methanol).

EXAMPLE 32

3-Hydrazino-5,6,7,8-tetrahydro-6-(2-n-propylvalcroyl)-pyrido[4,3-c]pyridazine 11.8 g of 3-chloro-5,6,7,8-tetrahydro-6-(2-n-propyl-valeroyl)pyrido[4,3-c]pyridazine and 40 cc of hydrazine hydrate are stirred at a bath temperature of 100° for 20 hours. The crude base, having a M.P. of 123°–126° (decomp.), is dissolved in methanol, and fumaric acid is added until the solution indicates a pH of 4, and boiling is effected for a short time. After cooling with ice the bis[3-hydrazino-5,6,7,8-tetrahydro-6-(2-n-propyl-valeroyl)pyrido[4,3-c]pyridazine]trisfumarate crystallizes. M.P. 96°–100° (decomp.).

The 3-chloro-5,6,7,8-tetrahydro-6-(2-n-propyl-valeroyl)pyrido[4,3-c]pyridazine, required as starting material, is produced in a manner analogous to that described in Example 8(g), from 3-chloro-5,6,7,8-tet-rahydropyrido[4,3-c]pyridazine maleate and 2-n-propylvaleroyl chloride. The organic phase is concentrated, and the crude product is extracted from the resulting solid residue with a Soxhlet extraction apparatus, and is recrystallized from cyclohexane. M.P. 94°–95°.

EXAMPLE 33

3-Hydrazino-6-hexahydrobenzoyl-5,6,7,8-tetrahy-dropyrido[4,3-c]pyridazine 8.6 g of 3-chloro-6-hexahydrobenzoyl-5,6,7,8-tet-rahydropyrido[4,3-c]pyridazine and 60 cc of hydrazine hydrate are stirred at a bath temperature of 100° for 2 hours. The crystalline crude base obtained upon cooling the reaction solution, is recrystallized from acetonitrile with the addition of purifying charcoal, and is dissolved together with 4 g of gentisic acid in 80 cc of absolute ethanol with heating. The gentisinate of the title compound crystallizes upon cooling the solution. M.P. 188°–190° (decomp.).

The 3-chloro-6-hexahydrobenzoyl-5,6,7,8-tetrahy-dropyrido[4,3-c]pyridazine, required as starting material, may be produced in a manner analogous to that described in Example 8(g), from 3-chloro-5,6,7,8-tet-rahydropyrido[4,3-c]pyridazine maleate and cyclohexanecarboxylic acid chloride. M.P. 144°–146° (decomp., from absolute ethanol).

EXAMPLE 34

6-(1-Adamantonyl)-3-hydrazino-5,6,7,8-tetrahy-dropyrido[4,3-c]pyridazine 8.1 g of 6-(1-adamantonyl)-3-chloro-5,6,7,8-tetrahy-dropyrido[4,3-c]pyridazine and 75 cc of hydrazine hydrate in 150 cc of dioxane are stirred at a bath temperature of 100° for 5 hours. The crude base is converted into bis[6-(1-adamantonyl)-3-hydrazino-5,6,7,8-tetrahy-dropyrido[4,3-c]pyridazino]trisfumarate with 2.8 g of fumaric acid in a solvent mixture of 50 cc of absolute ethanol and 25 cc of methanol. M.P. 140°–142° (decomp.).

The 6-(1-adamantonyl)-3-chloro-5,6,7,8-tetrahy-dropyrido[4,3-c]pyridazine, required as starting material, may be obtained in a manner analogous to that described in Example 8(g), from 3-chloro-5,6,7,8-tetrahydropyrido[4,3-c]pyridazino maleate and 1-adamantanecarboxylic acid chloride. M.P. 260°-261° (decomp., from dimethyl formamido).

EXAMPLE 35

6-Cyclobutanecarbonyl-3-hydrazino-5,6,7,8-tetrahydropyrido[4,3-c]pyridazine 13.4 g of 3-chloro-6-cyclobutyryl-5,6,7,8-tetrahydropyrido[4,3-c]pyridazine and 75 cc of hydrazine hydrate are stirred at a bath temperature of 100° for 1 hour. The oil obtained after concentrating the mixture in a vacuum is divided between water and chloroform/ethanol 9:1, and the organic phase is worked up as described in Example 10. The gentisinate of the title compound has a M.P. of 196°-198° decomp., from 95% ethanol/methanol 1:1).

The 3-chloro-6-cyclobutyryl-5,6,7,8-tetrahydropyrido[4,3-c]pyridazine, required as starting material, may be obtained in a manner analogous to that described in Example 8(g), from 3-chloro-5,6,7,8-tetrahydropyrido[4,3-c]pyridazine maleate and cyclobutanecarboxylic acid chloride. M.P. 104°-106° (decomp., from absolute ethanol).

EXAMPLE 36

3-Hydrazino-5,6,7,8-tetrahydro-6-pyrido[4,3-c]pyridazinecarboxylic acid ethyl ester 113 g of 3-chloro-5,6,7,8-tetrahydro-6-pyrido[4,3-c]pyridazinecarboxylic acid ethyl ester and 470 cc of hydrazine hydrate are stirred at reflux at a bath temperature of 110° for 1 hour. The title compound has a M.P. of 145°-147° (decomp., from absolute ethanol).

The 3-chloro-5,6,7,8-tetrahydro-6-pyrido[4,3-c]pyridazinecarboylic acid ethyl ester, required as starting material, may be produced in a manner analogous to that described in Example 4(e), from 300 g of 6-carbethoxy-5,6,7,8-tetrahydro-3(2H)pyrido[4,3-c]pyridazinone and 850 cc of phosphorous oxychloride. The crude product is recrystallized from 700 cc of absolute ethanol. M.P. 102°-105° (decomp.).

EXAMPLE 37

5,6,7,8-Tetrahydro-3-(1-methylhydrazino)-6-pyrido[4,3-c]pyridazinacarboxylic acid ethyl ester 72.6 g of 3-chloro-5,6,7,8-tetrahydro-6-pyrido[4,3-c]pyridazinecarboxylic acid ethyl ester are heated at reflux in 300 cc of methylhydrazine at a bath temperature of 110° for 1 hour while stirring, and the mixture is concentrated, the residue divided between chloroform and water and after concentrating the chloroform phase the title compound is obtained, M.P. 121°-123° (dec., from dimethoxyethane).

EXAMPLE 38

3-Hydrazino-5,6,7,8-tetrahydro-6-pyrido[4,3-c]pyridazinecarboxylic acid methyl ester 16.5 g of 3-chloro-5,6,7,8-tetrahydro-6-pyrido[4,3-c]pyridazinecarboxylic acid methyl ester and 70 cc of hydrazine hydrate are heated in a water bath for 1 hour. The title compound has a M.P. of 178°-180° (decomp., from acetonitrile).

The starting material may be produced as follows:

(a) A mixture of B 226.2 g of 1-methylpiperidone and 1 liter of benzene is added dropwise to a mixture heated to 70° of 378 g of chloroformic acid methyl ester and 2 liters of benzene within 100 minutes while passing a stream of nitrogen through the mixture. The mixture is subsequently stirred while boiling at reflux for 4½ hours. After cooling the mixture with ice, a small amount of precipitated crystalline material is filtered with suction, and the filtrate is concentrated in a vacuum. The resulting oil is distilled in a water pump vacuum. 1-Carbomethoxy-4-piperidone is obtained as main fraction at a B.P. of 128°-137° at 13 mm of Hg.

(b) 1,2,3,6-Tetrahydro-4-pyrrolidinylpyridine-1-carboxylic acid methyl ester: Produced in a manner analogous to that described in Example 4(a), from 420 g of 1-carbomethoxy-4-piperidone and 285 g of pyrrolidine. The crude product is purified by vacuum distillation. B.P. 200° at 0.01 mm of Hg.

(c) 1-Carbomethoxy-4-piperidone-3-acetic acid methyl ester: Produced in a manner analogous to that described in Example B 4(b), from 420.4 g of 1,2,3,6-tetrahydro-4-pyrrolidinylpyridine-1-carboxylic acid methyl ester and 306 g of bromoacetic acid methyl ester. Reaction time 13 hours. The crude product is purified by vacuum distillation. B.P. 220°-240° at 0.2 mm of Hg.

(d) 2,3,4,4a,5,6,7,8-Octahydro-3-oxo-6-pyrido[4,3-c]pyridazine carboxylic acid methyl ester: Produced in a manner analogous to that described in Example 4(c), from 45.8 g of 1-carbomethoxy-4-piperidone-3-acetic acid methyl ester and 10 g of hydrazine hydrate in 400 cc of absolute methanol and 20 cc of glacial acetic acid. M.P. 163°-165° (decomp., from benzene.

(e) 6-Carbomethoxy-5,6,7,8-tetrahydro-3(2H)pyrido[4,3-c]pyridazinone: Produced in a manner analogous to that described in Example 4(d), from 27.9 g of 2,3,4,4a,5,6,7,8-octahydro-3-oxo-6-pyrido[4,3-c]pyridazinecarboxylic acid methyl ester and 31.1 g of bromine. Reaction time 3 hours. After cooling, 100 cc of ice/water are added to the mixture, and the pH is adjusted to between 3 and 4 by the addition of 38 cc of a 10% aqueous caustic soda solution. The organic phase is separated and concentrated in a vacuum to a semicrystalline crude product. After recrystallization from methanol the compound has a M.P. of 192°-195° (decomp.).

(f) 3-Chloro-5,6,7,8-tetrahydro-6-pyrido[4,3-c]pyridazinocarboxylic acid methyl ester: Produced in a manner analogous to that described in Example 4(e), from 4.7 g of 6-carbomethoxy-5,6,7,8-tetrahydro-3(2H)pyrido[4,3-c]pyridazinone and 20 cc of phosphorus oxychloride. Purification by extraction with ligroin. M.P. 92°-94° (decomp.).

EXAMPLE 39

3-Hydrazino-5,6,7,8-tetrahydro-6-pyrido[1,3-c]pyridazinecarboxylic acid benzyl ester 19.2 g of crude oily 3-chloro-5,6,7,8-tetrahydro-B 6-pyrido[4,3-c]pyridazinecarboxylic acid benzyl ester and 100 cc of hydrazine hydrate are stirred at a bath temperature of 70° for 7½ hours, and the mixture is worked up to the crude title compound in a manner analogous to that described in Example 37, and this compound is recrystallized from acetonitrile.
M.P. 135°-137° (decomp.).

The 3-chloro-5,6,7,8-tetrahydro-6-pyrido [4,3-c]pyridazinecarboxylic acid benzyl ester, required as starting material, may be produced in a manner analogous to that described in Example 8(g), from 3-chloro-5,6,7,8-tetrahydropyrido[4,3-c]pyridazine maleate and chloroformic acid benzyl ester. The oily crude product is used as such for the next reaction.

EXAMPLE 40

3-Hydrazino-5,6,7,8-tetrahydro-6-pyrido[4,3-c]pyridazinecarboxylic acid allyl ester 23.4 g of crude oily 3-chloro-5,6,7,8-tetrahydro-6-pyrido[4,3-c]pyridazinecarboxylic acid allyl ester and 150 cc of hydrazine hydrate are heated at a bath temperature of 100° for 4 hours while stirring with the addition of 50 cc of dioxane. The yellow oil obtained after concentrating the mixture is taken up in chloroform and separated from the precipitated hydrazine hydrate. 20.6 g of the crude base obtained after concentrating the chloroform phase, are dissolved with 15.4 g of gentisic acid in 150 cc of absolute ethanol whilst hot. The crude gentisinate of the title compound crystallizes upon cooling the solution, and after recrystallization from methanol has a M.P. of 171°–173° (decomp.).

The 3-chloro-5,6,7,8-tetrahydro-6-pyrido [4,3-c]pyridazinecarboxylic acid allyl ester, required as starting material, may be obtained in a manner analogous to that described in Example 8(g), from 3-chloro-5,6,7,8-tetrahydropyrido[4,3-c]pyridazine maleate and chloroformic acid allyl ester. The oily crude product is used for the next reaction without purification.

EXAMPLE 41

3-Hydrazino-5,6,7,8-tetrahydro-6-pyrido[4,3-c]pyridazinecarboxylic acid ethyl ester A mixture of 1.7 g of 3-benzylmercapto-5,6,7,8-tetrahydro-6-pyrido[4,3-c]pyridazinecarboxylic acid ethyl ester, 1.3 g of hydrazine hydrate and 10 cc of 95% ethanol is heated at a bath temperature of 150° in an autoclave for 16 hours. The crude oil obtained upon concentrating the reaction solution in a vacuum, is divided between 70 cc of chloroform and 25 cc of a 10% aqueous caustic soda solution. The organic phase is concentrated, and the resulting oil is chromatographed on 40 g of silica gel. The title compound is eluted with chloroform/methanol 95:5. M.P. 145°–147° (decomp.).

The starting material may be obtained as follows:

(a) A solution of 12.1 g of 3-chloro-5,6,7,8-tetrahydro-6-pyrido[4,3-c]pyridazinecarboxylic acid ethyl ester and 4.2 g of thiourea in 200 cc of absolute ethanol is heated at reflux in an oil bath of 110° for two hours while stirring. The dark reaction solution is completely concentrated in a vacuum, and the resulting crude, semicrystalline 5,6,7,8-tetrahydro-3-mercapto-6-pyrido[4,3-c]pyridazinecarboxylic acid ethyl ester is crystallized from 200 cc of 95% ethanol.

M.P. 181°–183° (decomp., from 95% ethanol).

(b) A mixture of 13.2 g of benzyl bromide in 75 cc of dimethyl formamide is added dropwise within 2 hours to a suspension heated to 50° of 18.5 g of 5,6,7,8-tetrahydro-3-mercapto-6-pyrido[4,3-c]pyridazinecarboxylic acid ethyl ester and 12.8 g of potassium carbonate in 200 cc of dimethyl formamide. The mixture is subsequently stirred at the same temperature for 20 hours and is then completely concentrated in a vacuum. The residue is divided between 200 cc of chloroform and 50 cc of water, the organic phase is separated and concentrated to a dark oil in a vacuum. This is chromatographed on an aluminum oxide column, and elution is effected with a mixture of benzene/petroleum ether 2:1. The crude oily 3-benzylmercapto-5,6,7,8-tetrahydro-6-pyrido[4,3-c]pyridazinecarboxylic acid ethyl ester, obtained after concentrating the eluate, crystallizes from 75 cc of ether after the addition of 25 cc of petroleum ether.

M.P. 67°–63° (decomp.).

EXAMPLE 42

3-Hydrazino-5,6,7,8-tetrahydro-6-pyrido [4,3-c]pyridazinecarboxylic acid ethyl ester 3.8 g of 3-ethylmercapto-5,6,7,8-tetrahydro-6-pyrido[4,3-c]pyridazinecarboxylic acid ethyl ester and 3.6 g of hydrazine hydrate are reacted in accordance with the process described in Example 41. The oily crude product is crystallized from ethanol/ether. The title compound has a M.P. of 144°–146° (decomp., from 95% ethanol).

The 3-ethylmercapto-5,6,7,8-tetrahydro-6-pyrido[4,3-c]pyridazinecarboxylic acid ethyl ester, required as starting material, may be obtained in a manner analogous to that described in Example 41(b), from 5,6,7,8-tetrahydro-3-mercapto-6-pyrido[4,3-c]pyridazinecarboxylic acid ethyl ester and ethyl bromide.

M.P. 54°–56° from ligroin.

EXAMPLE 43

5,6,7,8-Tetrahydro-3-(1-methylhydrazino)-6-pyrido[4,3-c]pyridazinecarboxylic acid ethyl ester 4.8 g of 5,6,7,8-tetrahydro-3-mercaptopyrido[4,3-c]pyridazinecarboxylic acid ethyl ester and 20 cc of methyl hydrazine are stirred at a bath temperature of 100° for 1 hour. The title compound has a M.P. of 121°–123° (decomp., from dimethoxyethane).

EXAMPLE 44

6-Benzoyl-3-hydrazino-5,6,7,8-tetrahydropyrido[4,3-c]pyridazine

A solution of 2.7 g of 6-benzeyl-5,6,7,8-tetrahydro-3-mercaptopyrido[4,3-c]pyridazine in 30 cc of hydrazine hydrate is stirred at a bath temperature of 110° for 15 minutes. After 5 minutes a beige coloured precipitate results. After gas evolution is complete, the mixture is cooled with ice and the precipitated title compound is filtered off. The title compound has a M.P. of 220°–223° (decomp., from absolute ethanol).

The 6-benzoyl-5,6,7,8-tetrahydro-3-mercaptopyrido[4,3-c]pyridazine, required as starting material, may be obtained in a manner analogous to that described in Example 41(a), from 27.4 g of 6-benzoyl-3-chloro-5,6,7,8-tetrahydropyrido[4,3-c]pyridazine and 8.4 g of thiourea. After cooling the reaction mixture with ice, the compound precipitates. M.P. 225°–228° (decomp., from glacial acetic acid).

EXAMPLE 45

6-Benzoyl-3-hydrazine-5,6,7,8-tetrahydropyrido[4,3-c]pyridazine

A mixture of 3.3 g of 3-ethylmercapto-6-benzoyl-5,6,7,8-tetrahydropyrido[4,3-c]pyridazine and 15 cc of hydrazine hydrate in 15 cc of absolute ethanol is heated in an autoclave at a bath temperature of 150° for 14 hours. A maximum pressure of 13 atmospheres results. The oil obtained after concentrating the reaction mixture in a vacuum, is divided between chloroform and water, and the organic phase is concentrated to a semicrystalline residue. After recrystallization from dimethyl formamide, the title compound, having a M.P. of 220°–223° (decomp.), is obtained.

The 3-ethylmercapto-6-benzoyl-5,6,7,8-tetrahydropyrido[4,3-c]pyridazine, required as starting material, may be obtained in a manner analogous to that described in Example 41(b), from 34.8 g of 6-benzoyl-3-mercapto-5,6,7,8-tetrahydropyrido[4,3-c]pyridazine and 16.8 g of ethyl bromide. Reaction time 19 hours. Working up as described in Example 41 (b), eluant: benzene.

M.P. 132°–135° (decomp., from isopropanol/ether).

EXAMPLE 46

6-Benzoyl-3-hydrazine-5,6,7,8-tetrahydropyrido[4,3-c]pyridazine

A solution of 4.0 g of 3-benzylmercapto-6-benzoyl-5,6,7,8-tetrahydropyrido[4,3-c]pyridazine and 1.5 g of hydrazine hydrate in 10 cc of 95% ethanol is heated in an autoclave at a bath temperature of 150° for 16 hours. The oil obtained after concentrating the reaction mixture in a vacuum, is divided between chloroform and a small amount of water, and the organic phase is concentrated to a red oil. The title compound is obtained by crystallization from dimethyl formamide.

M.P. 220°–223° (decomp.).

The fumarate of the title compound, having a M.P. of 188°–190° (decomp.), is obtained by reacting the title compound with the calculated amount of fumaric acid in a small amount of 95% ethanol.

The 3-benzylmercapto-6-benzoyl-5,6,7,8-tetrahydropyrido[4,3-c]pyridazine, required as starting material, may be obtained in a manner analogous to that described in Example 41(b), from 6-benzoyl-3-mercapto-5,6,7,8-tetrahydropyrido[4,3-c]pyridazine and benzyl bromide. Purification by chromatography on aluminium oxide, eluant: benzene. M.P. 114°–116° (decomp., from ether).

EXAMPLE 47

6-Benzoyl-5,6,7,8-tetrahydro-3-(1-methylhydrazino)-pyrido[4,3-c]pyridazine

A solution of 3.4 g of 6-benzoyl-5,6,7,8-tetrahydro-3-mercaptopyrido[4,3-c]pyridazine in 40 cc of methylhydrazine is stirred at a bath temperature of 110° for 1½ hours. The oil obtained after concentrating the mixture in a vacuum is taken up in absolute ethanol, and the calculated amount of gentisic acid is added. After standing for some time the crystalline bisgentisinate of the title compound is obtained.

M.P. 166°–168° (decomp.).

EXAMPLE 48

6-Benzoyl-5,6,7,8-tetrahydro-3-(1-methylhydrazino)-pyrido[4,3-c]pyridazine 2.9 g of 6-benzoyl-5,6,7,8-tetrahydro-3-methylmercaptopyrido[4,3-c]pyridazine and 1.5 g of methylhydrazine are heated in 20 cc of 95% ethanol in an autoclave at a bath temperature of 150° for 18 hours, and the mixture is subsequently worked up as described in Example 47. The biscentisinate of the title compound has a M.P. of 166°–168° (decomp.).

The 6-benzoyl-5,6,7,8-tetrahydro-3-methylmercaptopyrido[4,3-c]pyridazine, used as starting material, may be obtained in a manner analogous to that described in Example 41(b), from 34.8 g of 6-benzoyl-5,6,7,8-tetrahydro-3-mercaptepyrido[4,3-c]pyridazine and 21.9 g of methyl iodide. Working up is effected in a manner analogous to that described in Example 41(b), eluant: chloroform. M.P. 143°–145° (decomp., from 95% ethanol).

EXAMPLE 49

3-Hydrazine-5,6,7,8-tetrahydro-6-((Z)-2-methyl-2-butenoyl)pyrido[4,3-c]pyridazine A suspension of 12.6 g of 3-chloro-5,6,7,8-tetrahydro-6-((Z)-2-methyl-2-butenoyl)pyrido[4,3-c]pyridazine in 50 cc of hydrazine hydrate is stirred at a bath temperature of 100° for 30 minutes, and the mixture is subsequently worked up as described in Example 4. The bis[3-hydrazino-5,6,7,8-tetrahydro-6-((Z)-2-methyl-2-butenoyl)pyrido[4,3-c]pyridazine] trisfumarate has a M.P. of 159°–160° (decomp., from absolute ethanol).

The 3-chloro-5,6,7,8-tetrahydro-6-((Z)-2-methyl-2-butenoyl)pyrido[4,3-c]pyridazine, required as starting material, may be produced in a manner analogous to that described in Example 8 (g), from 3-chloro-5,6,7,8-tetrahydropyrido[4,3-c]pyridazine maleate and (Z)-2-methyl-2-butenoyl chloride. M.P. 95°–96° (decomp., from cyclohexane).

EXAMPLE 50

3-Hydrazino-5,6,7,8-tetrahydro-6-(4-pentenoyl)-pyrido[4,3-c]pyridazine 12.3 g of 3-chloro-5,6,7,8-tetrahydro-6-(4-pentenoyl)-pyrido[4,3-c]pyridazine are stirred in 40 cc of hydrazine hydrate at a bath temperature of 90° for 3 hours. The mixture is cooled with ice, 100 cc of chloroform are added, and the excess hydrazine is separated. Upon concentrating the chloroform phase, the crude title compound is obtained as an oil. This is converted to bis[3-hydrazino-5,6,7,8-tetrahydro-6-(4-pentenoyl)-pyrido[4,3-c]pyridazine]trisfumarate by boiling with 4 g of fumaric acid in 50 cc of absolute ethanol. M.P. 132°–134° (decomp., from absolute ethanol).

The 3-chloro-5,6,7,8-tetrahydro-6-(4-pentenoyl)-pyrido[4,3-c]pyridazine, required as starting material, may be obtained in a manner analogous to that described in Example 8(g), from 3-chloro-5,6,7,8-tetrahydropyrido[4,3-c]pyridazine maleate and 4-pentenoyl chloride. M.P. 90°–92° (decomp., from carbon tetrachloride.

EXAMPLE 51

5,6,7,8-Tetrahydro-3-(1-methylhydrazino)-6-(4-pentenoyl)pyrido[4,3-c]pyridazine 12.3 g of 3-chloro-5,6,7,8-tetrahydro-6-(4-pentenoyl)-pyrido[4,3-c]pyridazine and 50 cc of methylhydrazine are stirred at a bath temperature of 90° for 30 minutes. The crude title compound is obtained in crystalline form upon cooling the mixture with ice. The title compound has a M.P. of 128°–130° (decomp., from isopropanol).

EXAMPLE 52

3-Hydrazino-5,6,7,8-tetrahydro-6-pyrido[4,3-c]pyridazinecarboxylic acid phenyl ester A solution of 20.3 g of crude oily 3-chloro-5,6,7,8-tetrahydro-6-pyrido[4,3-c]pyridazinecarboxylic acid phenyl ester in 100 cc of hydrazine hydrate is stirred in an oil bath of 100° for 1½ hours. The reaction solution is concentrated in a vacuum and the residue is divided between 225 cc of chloroform and 25 c of water. The crude title compound is obtained as semicrystalline residue upon concentrating the organic phase in a vacuum.

The 3-chloro-5,6,7,8-tetrahydro-6-pyrido[4,3-c]pyridazinecarboxylic acid phenyl ester, required as starting material, may be produced in a manner analogous to that described in Example 8(g), from 3-chloro-5,6,7,8-tetrahydropyrido[4,3-c]pyridazine maleate and chloroformic acid phenyl ester. The oily crude product is used as such for the next reaction.

EXAMPLE 53

3-Hydrazino-5,6,7,8-tetrahydro-8-methyl-6-pyrido[4,3-c]pyridazinecarboxylic acid ethyl ester 14.3 g of crude 3-chloro-5,6,7,8-tetrahydro-8-methyl-6-pyrido[4,3-c]pyridazinecarboxylic acid ethyl ester are stirred in 50 cc of hydrazine hydrate at a bath temperature of 100° for 2½ hours, the mixture is worked up to the crude base as described in Example 17, and this base is reacted with fumaric acid as described in Example 4. Bis(3-hydrazino-5,6,7,8-tetrahydro-8-methyl-6-pyrido[4,3-c]pyridazinecarboxylic acid ethyl ester)trisfumarate alcoholate has a M.P. of 171°–174° (decomp., from 95% ethanol).

The starting material may be produced as follows:

(a) A mixture of 25.4 g of 1,3-dimethyl-4-piperidone and 250 cc of absolute benzene is added dropwise to a mixture of 65.2 g of chloroformic acid ethyl ester in 250 cc of absolute benzene, at room temperature, within 30 minutes while stirring, and the reaction mixture is subsequently heated to the boil at reflux for 4 hours. The mixture is cooled with ice, a small amount of precipitated material is filtered with suction, and the filtrate is extracted thrice with 200 cc amounts of 20% aqueous sodium chloride solution. The organic phase is concentrated in a vacuum, and the resulting 1-carbethoxy-3-methyl-4-piperidone is purified by distillation. B.P. 71°–75° at 0.08 mm of Hg.

(b) 1,2,3,6-Tetrahydro-3-methyl-4-pyrrolidinylpyridine-1-carboxylic acid ethyl ester: Produced in a manner analogous to that described in Example 4(a), from 92.2 g of 1-carbethoxy-3-methyl-4-piperidone and 53.5 g of pyrrolidine. The oily crude product is used as such for the next reaction.

(c) 1-Carbethoxy-3-methyl-4-piperidone-5-acetic acid ethyl ester: Produced in a manner analogous to that described in Example 4(b), from 125 g of crude 1,2,3,6-tetrahydro-3-methyl-4-pyrrolidinylpyridine-1-carboxylic acid ethyl ester and 83.5 g of bromoacetic acid ethyl ester. The crude product is purified by distillation. B.P. 144°–149° at 0.2 mm of Hg.

(d) 2,3,4,4a,5,6,7,8-Octahydro-8-methyl-3-oxo-6-pyrido[4,3-c]pyridazinecarboxylic acid ethyl ester: Produced in a manner analogous to that described in Example 4(c), from 27.1 g of 1-carbethoxy-3-methyl-4-piperidone-5-acetic acid ethyl ester and 5 g of hydrazine hydrate. M.P. 101°–103° (decomp., from ether).

(e) 6-Carbethoxy-5,6,7,8-tetrahydro-8-methyl-3(2H)pyrido[4,3-c]pyridazinone: Produced in a manner analogous to that described in Example 4(d), from 15.5 g of 2,3,4,4a,5,6,7,8-octahydro-8-methyl-3-oxo-6-pyrido[4,3-c]pyridazinecarboxylic acid ethyl ester and 10.4 g of bromine. After cooling to room temperature, 100 g of ice/water are added to the mixture, the organic phase is separated and concentrated in a vacuum to an oily crude product, which crystallizes after the addition of ether. M.P. 125°–127° (decomp., from ether).

(f) 3-Chloro-5,6,7,8-tetrahydro-8-methyl-6-pyrido[4,3-c]pyridazinecarboxylic acid ethyl ester: Produced in a manner analogous to that described in Example 4(e), from 11.0 g of 6-carbethoxy-5,6,7,8-tetrahydro-8-methyl-3(2H)pyrido[4,3-c]pyridazinone and 50 cc of phosphorus oxychloride. The oily crude product is used as such for the next reaction.

EXAMPLE 54

5,6,7,8-Tetrahydro-3-(1-methylhydrazino)-6-pyrido[4,3-c]pyridazinecarboxylic acid ethyl ester A solution of 4.8 g of 5,6,7,8-tetrahydro-3-mercapto-6-pyrido[4,3-c]pyridazinecarboxylic acid ethyl ester in 20 cc of methylhydrazine is stirred at a bath temperature of 100° for 1 hour. The reaction solution is cooled with ice, and the precipitated reaction product is filtered off. The title compound has a M.P. of 121°–123° (decomp., from dimethoxyethane).

EXAMPLE 55

3-Hydrazino-6-(p-phenylbenzyl)-5,6,7,8-tetrahydropyrido[4,3-c]pyridazine 9.0 g of 3-chloro-6-(p-phenylbenzoyl)-5,6,7,8-tetrahydropyrido[4,3-c]pyridazine and 55 cc of hydrazine hydrate and stirred at a bath temperature of 100° for 5½ hours. After cooling the mixture with ice the title compound precipitates and is recrystallized from 200 cc of dimethyl formamide. M.P. 241°–244° (decomp.).

The 3-chloro-6-(p-phenylbenzoyl-5,6,7,8-tetrahydropyrido[4,3-c]pyridazine, required as starting material, may be obtained in a manner analogous to that described in Example 8(g), from 23.6 g of 3-chloro-5,6,7,8-tetrahydropyrido[4,3-c]pyridazine maleate and 21.7 g of p-phenylbenzoyl chloride. M.P. 159°–162° (decomp., from 95% ethanol).

EXAMPLE 56

3-Hydrazino-5,6,7,8-tetrahydro-6-(o-methylmercaptobenzoyl)pyrido[4,3-c]pyridazine 23.1 g of 3-chloro-5,6,7,8-tetrahydro-6-(o-methylmercaptobenzoyl)pyrido[4,3-c]pyridazine are stirred in 100 cc of hydrazine hydrate at a bath temperature of 100° for 2 hours, and the reaction mixture is worked up as described in Example 17. The gentisinato of the title compound has a M.P. of 172°–175°.

The 3-chloro-5,6,7,8-tetrahydro-6-(o-methylmercaptobenzoyl)pyrido[4,3-c]pyridazine, required as starting material, may be obtained in a manner analogous to that described in Example 8(g), from 28.6 g of 3-chloro-5,6,7,8-tetrahydropyrido[4,3-c]pyridazine maleate and 19.6 g of o-methylmercaptobenzoyl chloride. M.P. 120°–123° (decomp., from isopropanol/methanol).

EXAMPLE 57

6-Benzoyl-3-cyclohexylidenehydrazino-5,6,7,8-tetrahydropyrido[4,3-c]pyridazine

A suspension of 8.3 g of 6-benzoyl-3-hydrazino-5,6,7,8-tetrahydropyrido[4,3-c]pyridazne in 20 cc of cyclohexanone is boiled at reflux at a bath temperature of 180° for 2 hours. The title compound has a M.P. of 188°–191° (decomp., from acetonitrile).

EXAMPLE 58

3-Isopropylidenehydrazino-5,6,7,8-tetrahydro-6-phenacetylpyrido[4,3-c]pyridazine

9.6 g of crude oily 3-hydrazino-5,6,7,8-tetrahydro-6-phenacetylpyrido[4,3-c]pyridazine are heated with 20 cc of acetone on a water bath for 15 minutes. The title compound has a M.P. of 195°–196° (decomp., from methanol).

The starting material may be obtained as follows:

(a) 3-Chloro-5,6,7,8-tetrahydro-6-phenacetylpyrido[4,3-c]pyridazine: Produced in a manner analogous to that described in Example 8(g), from 57.0 g of 3-chloro-5,6,7,8-tetrahydropyrido[4,3-c]pyridazine maleate and 46.6 g of phenylacetic acid chloride.

M.P. 156°–157° (decomp., from absolute ethanol).

(b) 3-Hydrazino-5,6,7,8-tetrahydro-6-phenacetylpyrido[4,3-c]pyridazine: Produced in a manner analogous to that described in Example 8, from 19.5 g of 3-chloro-5,6,7,8-tetrahydro-6-phenacetylpyrido[4,3-c]pyridazine and 70 cc of hydrazine hydrate with the addition of 70 cc of isopropanol. Eath temperature 100°, reaction time 5 hours. The crude product obtained after working up is used as such for the next reaction.

EXAMPLE 59

6-(p-Chlorobenzoyl)-3-isopropylidenehydrazino-5,6,7,8-tetrahydropyrido[4,3-c]pyridazine

A suspension of 3.1 g of crude 6-(p-chlorobenzoyl)-3-hydrazino-5,6,7,8-tetrahydropyrido[4,3-c]pyridazine in 30 cc of acetone is heated on a water bath for 1 hour. The title compound has a M.P. of 221°–223° (decomp., from ethanol).

The starting material may be produced as follows:

(a) 3-Chloro-6-(p-chlorobenzoyl)-5,6,7,8-tetrahydropyrido[4,3-c]pyridazino: Produced in a manner analogous to that described in Example 8(g), from 3-chloro-5,6,7,8-tetrahydropyrido[4,3-c]pyridazine maleate and p-chlorobenzoyl chloride. Reaction time 24 hours at room temperature. M.P. 170°–172° (decomp., from absolute ethanol).

(b) 6-(p-Chlorobenzoyl)-3-hydrazino-5,6,7,8-tetrahydropyrido[4,3-c]pyridazine: Produced in a manner anlogous to that described in Example 8, from 15.4 g of 3-chloro-6-(p-chlorobenzoyl)-5,6,7,8-tetrahydropyrido[4,3-c]pyridazine and 50 cc of hydrazine hydrate with the addition of 40 cc of dioxane. Reaction time 9½ hours at a bath temperature of 80°, and 7 hours at room temperature. The crystalline compound is used for the next reaction in crude state.

EXAMPLE 60

6-(3,3-Diphenylpropionyl)-3-isopropylidenehydrazino-5,6,7,8-tetrahydropyrido[4,3-c]pyridazine

A solution of 1.5 g of 6-(3,3-diphenylpropionyl)-3-hydrazino-5,6,7,8-tetrahydropyrido[4,3-c]pyridazine in 40 cc of absolute acetone is heated on a water bath for 35 minutes. The title compound has a M.P. of 172°–175° (decomp., from absolute ethanol).

EXAMPLE 61

6-(2,4-Dichlorobenzoyl)-3-isopropylidenehydrazino-5,6,7,8-tetrahydropyrido[4,3-c]pyridazine

A solution of 1.2 g of crude 6-(2,4-dichlorobenzoyl)-3-hydrazino-5,6,7,8-tetrahydropyrido[4,3-c]pyridazine in 5 cc of acetone is heated on a water bath for 5 minutes. The title compound has a M.P. of 211°–214° (decomp., from methanol).

EXAMPLE 62

3-(2-Butylidenehydrazino)-5,6,7,8-tetrahydro-6-pyristinoylpyrido[4,3-c]pyridazino

A solution of 5.2 g of 3-hydrazino-5,6,7,8-tetrahydro-6-myristinoylpyrido[4,3-c]pyridazine in 50 cc of methylethyl ketone is heated to the boil at reflux for 4 hours while stirring. The title compound has a M.P. of 83°–85° (decomp., from cyclohexane).

EXAMPLE 63

3-(3-Pentylidenehydrazino)-6-pivaloyl-5,6,7,8-tetrahydropyrido[4,3-c]pyridazine

1 g of 3-hydrazino-5,6,7,8-tetrahydro-6-pivaloylpyrido[4,3-c]pyridazine is suspended in 10 cc of diethylketone, and heating on a water bath is effected for 1 hour. The title compound has a M.P. of 183°–185° (decomp., from absolute ethanol).

EXAMPLE 64

6-Butyryl-3-isopropylidenehydrazino-5,6,7,8-tetrahydropyrido[4,3-c]pyridazine

A solution of 3.5 g of crude oily 6-butyryl-3-hydrazino-5,6,7,8-tetrahydropyrido[4,3-c]pyridazine in 20 cc of acetone is heated to the boil at reflux on a water bath for 20 minutes. The title compound has a M.P. of 152°–154° (decomp., from acetone).

EXAMPLE 65

3-Isopropylidenehydrazino-6-octanoyl-5,6,7,8-tetrahydropyrido[4,3-c]pyridazine

A solution of 3.5 g of crude semicrystalline 3-hydrazino-6-octanoyl-5,6,7,8-tetrahydropyrido[4,3-c]pyridazine in 50 cc of acetone is heated to the boil at reflux while stirring for 30 minutes. The title compound has a M.P. of 118°–121° (decomp., from light gasoline).

EXAMPLE 66

5,6,7,8-Tetrahydro-8-isopropylidenehydrazino-6-pyrido[4,3-c]pyridazinecarboxylic acid ethyl ester

A suspension of 23.7 g of 3-hydrazino-5,6,7,8-tetrahydro-6-pyrido[4,3-c]pyridazinecarboxylic acid ethyl ester in 100 cc of acetone is heated at reflux for 4 hours while stirring. The title compound has a M.P. of 171°–174° (decomp., from methanol).

EXAMPLE 67

3-(2-Butylidenehydrazino)-5,6,7,8-tetrahydro-6-pyrido[4,3-c]pyridazinecarboxylic acid ethyl ester

A suspension of 23.7 g of 3-hydrazino-5,6,7,8-tetrahydro-6-pyrido[4,3-c]pyridazinecarboxylic acid ethyl ester in 100 cc of methylethyl ketone is heated at reflux for 4 hours while stirring. The title compound has a M.P. of 142°–146° (decomp., from methanol).

EXAMPLE 68

5,6,7,8-Tetrahydro-3-isopropylidenehydrazino-6-pyrido[4,3-c]pyridazinecarboxylic acid allyl ester

A solution of 4 g of 3-hydrazino-5,6,7,8-tetrahydro-6-pyrido[4,3-c]pyridazinecarboxylic acid allyl ester in 40 cc of acetone is heated at reflux on a water bath for 30 minutes. The title compound has a M.P. of 134°–136° (decomp.).

EXAMPLE 69

3-Cyclohexylidenehydrazino-5,6,7,8-tetrahydro-6-(p-toluoyl)pyrido[4,3-c]pyridazine 1.0 g of 3-hydrazino-5,6,7,8-tetrahydro-6-(p-toluoyl)-pyrido[4,3-c]pyridazine and 10 cc of cyclohexanone are heated at reflux in an oil bath of 180° for 1 hour. The title compound has a M.P. of 208°-210° (decomp., from 95% ethanol).

EXAMPLE 70

6-(o-Fluorobenzoyl)-5,6,7,8-tetrahydro-3-isopropylidenehydrazinopyrido[4,3-c]pyridazine 1.0 g of 6-(o-fluorobenzoyl)-3-hydrazino-5,6,7,8-tetrahydropyrido[4,3-c]pyridazine is heated in 10 cc of acetone on a water bath at reflux for 30 minutes. The title compound has a M.P. of 200°-203° (decomp., from absolute ethanol).

EXAMPLE 71

6-Cyclobutanecarbonyl-3-isopropylidenehydrazino-5,6,7,8-tetrahydropyrido[4,3-c]pyridazine A solution of 5.8 g of 6-cyclobutanecarbonyl-3-hydrazino-5,6,7,8-tetrahydropyrido[4,3-c]pyridazine in 50 cc of acetone and 2 drops of glacial acetic acid is heated at reflux on a water bath for 30 minutes. The crude product obtained as a brown oil is crystallized with absolute ethanol. The title compound has a M.P. of 175°-178° (decomp., from acetone/ether).

EXAMPLE 72

6-Benzoyl-3-cyclododecanylidenehydrazino-5,6,7,8-tetrahydropyrido[4,3-c]pyridazine A suspension of 2.7 g of 6-benzoyl-3-hydrazino-5,6,7,8-tetrahydropyrido[4,3-c]pyridazino and 1.8 g of cyclododecanone in 20 cc of absolute ethanol is heated on a water bath for 30 minutes, whereby a dissolution and reprecipitation clearly occurs. The resulting title compound is recrystallized from a mixture of 160 cc of methanol and 30 cc of dimethyl formamide. M.P. 222°-225° (decomp.).

EXAMPLE 73

3-(2-Butylidenehydrazino)-6-(p-phenylbenzoyl)-5,6,7,8-tetrahydropyrido[4,3-c]pyridazine 0.5 g of 3-hydrazino-6-(p-phenylbenzoyl)-5,6,7,8-tetrahydropyrido[4,3-c]pyridazine are heated in 5 cc of methylethyl ketone on a water bath for 1 hour. The title compound has a M.P. of 260°-262° (decomp., from methylethyl ketone).

EXAMPLE 74

5,6,7,8-Tetrahydro-3-isopropylidenehydrazino-8-methyl-6-pyrido[4,3-c]pyridazinocarboxylic acid ethyl ester A solution of 1 g of bis(3-hydrazino-5,6,7,8-tetrahydro-8-methyl-6-pyrido[4,3-c]pyridazine) trisfumarate alcoholate in 10 cc of acetone is heated on a water bath for 15 minutes. The reaction mixture is cooled with ice, and the title compound which crystallizes is divided between 100 cc of chloroform and 5 cc of concentrated aqueous ammonia solution, the chloroform phase is separated and concentrated. The title compound has a M.P. of 140°-142° (decomp., from absolute ethanol).

EXAMPLE 75

5,6,7,8,9,10,11,12,13,14-Decahydro-3-isopropylidenehydrazinocyclododeca[c]pyridazine 1.5 g of 3-hydrazino-5,6,7,8,9,10,11,12,13,14-decahydrocyclododeca[c]pyridazine fumarate are heated in 20 cc of acetone, to which a few drops of concentrated aqueous ammonia solution have been added, on a water bath for 1 hour. The mixture is cooled with ice, and the resulting crude title compound is divided between 5 cc of concentrated aqueous caustic soda solution and 20 cc of chloroform. The chloroform phase is concentrated, whereby a yellowish foam results, from which the title compound is obtained by recrystallization from absolute ethanol. M.P. 165°-166° (decomp.).

EXAMPLE 76

5,6,7,8,9,10-Hexahydro-3-isopropylidenehydrazinocycloocta[c]pyridazine

A solution of 0.5 g of 3-hydrazino-5,6,7,8,9,10-hexahydrocycloocta[c]pyridazine in 15 cc of absolute acetone is heated on a water bath for 1 hour. After cooling the title compound crystallizes.

M.P. 165°-167° (decomp.).

EXAMPLE 77

3-Cyclohexylidenehydrazino-5,6,7,8,9,10-hexahydrocycloocta[c]pyridazine

A solution of 10.0 g of 3-hydrazino-5,6,7,8,9,10-hexahydrocycloocta[c]pyridazine in 100 cc of cyclohexanone is boiled at reflux at a bath temperature of 180° for 1 hour and 45 minutes. The mixture is concentrated in a vacuum, whereby the crystalline title compound is obtained and is recrystallized from isopropanol. M.P. 160°-162° (decomp.).

EXAMPLE 78

6-Benzoyl-3-isopropylidenehydrazino-5,6,7,8-tetrahydropyrido[4,3-c]pyridazine

A solution of 0.5 g of 6-benzoyl-3-hydrazino-5,6,7,8-tetrahydropyrido[4,3-c]pyridazine in 15 cc of absolute acetone, to which 4 drops of glacial acetic acid have been added, is heated on a water bath for 1 hour. The solution is concentrated in a vacuum, and the crude title compound, obtained as an oil, is crystallized with ether. The title compound has a M.P. of 185°-190° (decomp.).

EXAMPLE 79

6-Benzoyl-3-(2-butylidenehydrazino)-5,6,7,8-tetrahydropyrido[4,3-c]pyridazine

A suspension of 13.5 g of 6-benzoyl-3-hydrazino-5,6,7,8-tetrahydropyrido[4,3-c]pyridazine in 100 cc of methylethyl ketone is heated at reflux while stirring for 4 hours. The title compound has a M.P. of 191°-193°, from 95% ethanol.

EXAMPLE 80

3-Hydrazino-5,6,7,8,9,10-hexahydrocycloocta[c]pyridazine

A solution of 10.1 g of 3-mercapto-5,6,7,8,9,10-hexahydrocycloocta[c]pyridazine in 75 cc of hydrazine hydrate and 50 cc of dioxane is heated at a bath temperature of 110° while stirring for 24 hours. Upon cooling the reaction mixture, the title compound precipitates and is purified by washing with a small amount of water and recrystallizing from 95% ethanol. The title compound has a M.P. of 145°-148° (decomp., from absolute ethanol).

The starting material may be produced as follows:

59.1 g of 3-chloro-5,6,7,8,9,10-hexahydrocycloocta[c-]pyridazine and 25.2 g of thiourea are heated at reflux in 250 cc of absolute ethanol while stirring for 20 hours. The reaction mixture is subsequently concentrated and divided between chloroform and water. After concentrating the chloroform phase, crude 3-mercapto-5,6,7,8,9,10-hexahydrocycloocta[c]pyridazine is obtained and is recrystallized from 250 cc of absolute ethanol with the addition of carbon.

M.P. 167°-170° (decomp.).

EXAMPLE 81

Using the procedure described in Example 75 the following compounds of formula Ib are obtained from the corresponding compound of formula Ia,

| | A | $R_3$ | $R_4$ | $R_2$ | $R_8$ | $R_9$ |
|---|---|---|---|---|---|---|
| (a) | —$CH_2$— | —$(CH_2)_{12}$— | | —$CH_3$ | H | 8-tBu |
| (b) | —CH*— | —$CH_3$ | —$CH_3$ | H | 6-$CH_3$ | 8-$CH_3$ |

*$R_8$ is bound to A

What is claimed is:

1. A pharmaceutical composition useful in the treatment of hypertension comprising an antihypertensive effective amount of a compound of the formula:

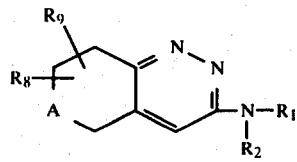

wherein
$R_1$ is amino or

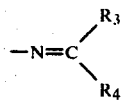

wherein each of
$R_3$ and $R_4$ is alkyl of 1 to 4 carbon atoms, or
$R_3$ and $R_4$ together with the carbon atom to which they are bound form cycloalkylidene of 5 to 12 carbon atoms,
$R_2$ is hydrogen or methyl,
A is —$(CH_2)_n$—
wherein n is 0 or an integer from 1 to 7 or >N—CO—$R_5$
wherein $R_5$ is alkyl of 1 to 16 carbon atoms, alkenyl of 3 to 6 carbon atoms, cycloalkyl of 3 to 8 carbon atoms, 1-adamantyl, or —$(CH_2)_m$—$R_6$,
wherein
m is 0 or an integer from 1 to 4, and
$R_6$ is phenyl; phenyl monosubstituted by fluorine, chlorine, bromine, alkyl or alkoxy of 1 to 4 carbon atoms, alkylmercapto of 1 to 4 carbon atoms, or phenyl; phenyl substituted by two or three substituents selected from the group consisting of chlorine, alkyl or alkoxy of 1 to 4 carbon atoms; diphenylmethyl, the phenyl rings of which may be monosubstituted by fluorine, chlorine, bromine, alkyl or alkoxy of 1 to 4 carbon atoms; or naphthyl or —$OR_7$,
wherein $R_7$ is alkyl of 1 to 4 carbon atoms, alkenyl of 2 to 4 carbon atoms or phenyl or phenyl alkyl which may be monosubstituted on the phenyl ring by chlorine; alkyl or alkoxy or 1 to 4 carbon atoms, and in which the alkylene chain of phenylalkyl is of 1 to 4 carbon atoms, and
$R_8$ and $R_9$ are each hydrogen or alkyl of 1 to 4 carbon atoms,
provided that when $R_6$ is phenyl substituted with more than one tertiary butyl or tertiary butoxy, they are on other than adjacent carbon atoms,
or pharmaceutically acceptable acid addition salts thereof in association with a pharmaceutical carrier.

2. A pharmaceutical composition according to claim 1, useful in the treatment of hypertension comprising 1.3 to 350 milligrams of the compound per unit dosage.

3. A pharmaceutical composition according to claim 1, in which $R_1$ is amino.

4. A pharmaceutical composition according to claim 1, in which $R_1$ is

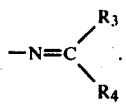

5. A pharmaceutical composition according to claim 1, in which A is —$(CH_2)_n$—.

6. A pharmaceutical composition according to claim 1, in which A is >N—$COR_5$.

7. A pharmaceutical composition according to claim 1, in which the compound is 6-benzoyl-3-hydrazino-5,6,7,8-tetrahydropyrido[4,3-c]pyridazine.

8. A pharmaceutical composition according to claim 1, in the form of a tablet, dragee or capsule.

9. A method of treating hypertension in warm blooded animals which comprises orally administering to an animal in need of such treatment a therapeutically effective amount of a compound of the formula

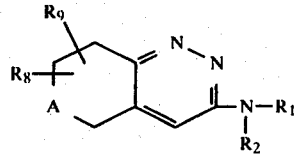

wherein
$R_1$ is amino or

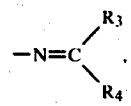

wherein each of
$R_3$ and $R_4$ is alkyl of 1 to 4 carbon atoms, or
$R_3$ and $R_4$ together with the carbon atom to which they are bound, form cycloalkylidene of 5 to 12 carbon atoms,
$R_2$ is hydrogen or methyl, A is —(CH$_2$)$_n$—
  wherein n is 0 or an integer from 1 to 7 or >N—CO—R$_5$
  wherein R$_5$ is alkyl of 1 to 16 carbon atoms, alkenyl of 3 to 6 carbon atoms, cycloalkyl of 3 to 8 carbon atoms, 1-adamantyl, or —(CH$_2$)$_m$—R$_6$,
  wherein
    m is 0 or an integer from 1 to 4, and
    R$_6$ is phenyl; phenyl monosubstituted by fluorine, chlorine, bromine, alkyl or alkoxy of 1 to 4 carbon atoms, alkyl-mercapto of 1 to 4 carbon atoms, or phenyl; phenyl substituted by two or three substituents selected from the group consisting of chlorine, alkyl or alkoxy of 1 to 4 carbon atoms; diphenylmethyl, the phenyl rings of which may be monosubstituted by fluorine, chlorine, bromine, alkyl or alkoxy of 1 to 4 carbon atoms; or naphthyl or —OR$_7$,
      wherein R$_7$ is alkyl of 1 to 4 carbon atoms, alkenyl of 2 to 4 carbon atoms or phenyl or phenylalkyl which may be monosubstituted on the phenyl ring by chlorine; alkyl or alkoxy of 1 to 4 carbon atoms, and in which the alkylene chain of phenylalkyl is of 1 to 4 carbon atoms, and
R$_8$ and R$_9$ are each hydrogen or alkyl of 1 to 4 carbon atoms,
provided that when R$_6$ is phenyl substituted with more than one tertiary butyl or tertiary butoxy, they are on other than adjacent carbon atoms,
or a pharmaceutically acceptable acid addition salt thereof.

10. A method according to claim 9, in which 5 to 700 milligrams of the compound are orally administered daily.

11. A method according to claim 9, in which 1.3 to 350 milligrams of the compound are administered orally per unit dose.

12. A method according to claim 9, in which R$_1$ is amino.

13. A method according to claim 9, in which R$_1$ is

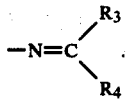

14. A method according to claim 9, in which A is —(CH$_2$)$_n$—.

15. A method according to claim 9 in which A is >N—COR$_5$.

16. A method according to claim 9, in which the compound is 6-benzoyl-3-hydrazino-5,6,7,8-tetrahydropyrido[4,3-c]pyridazine.

17. A method according to claim 9, in which the compound is 3-hydrazino-5,6,7,8-tetrahydro-6-(3-phenylpropionyl)pyrido[4,3-c]pyridazine.

* * * * *